(12) United States Patent
Benjamin

(10) Patent No.: US 9,381,381 B2
(45) Date of Patent: Jul. 5, 2016

(54) TREATMENT OF NAIL INFECTIONS WITH NO

(75) Inventor: Nigel Benjamin, London (GB)

(73) Assignee: Aberdeen University, Aberdeen (GB)

( * ) Notice: Subject to any disclaimer, the term of this patent is extended or adjusted under 35 U.S.C. 154(b) by 1773 days.

(21) Appl. No.: 12/455,141

(22) Filed: May 28, 2009

(65) Prior Publication Data

US 2010/0015253 A1   Jan. 21, 2010

Related U.S. Application Data

(63) Continuation of application No. 10/484,321, filed as application No. PCT/GB02/03575 on Aug. 2, 2002, now abandoned.

(30) Foreign Application Priority Data

Aug. 3, 2001   (GB) .................................. 0119011.5

(51) Int. Cl.

| | |
|---|---|
| *A61K 31/04* | (2006.01) |
| *A61K 33/00* | (2006.01) |
| *A61K 47/12* | (2006.01) |
| *A61K 47/32* | (2006.01) |
| *A61K 47/38* | (2006.01) |
| *A61K 8/19* | (2006.01) |
| *A61Q 3/00* | (2006.01) |
| *A61K 9/00* | (2006.01) |

(52) U.S. Cl.
CPC ... *A61Q 3/00* (2013.01); *A61K 8/19* (2013.01); *A61K 9/0012* (2013.01); *A61K 31/04* (2013.01); *A61K 33/00* (2013.01); *A61K 47/12* (2013.01); *A61K 47/32* (2013.01); *A61K 47/38* (2013.01)

(58) Field of Classification Search
CPC ....... A61K 31/04; A61K 33/00; A61K 47/12; A61K 47/32; A61K 47/38; A61K 8/19; A61K 9/0012; A61Q 3/00
See application file for complete search history.

(56) References Cited

U.S. PATENT DOCUMENTS

| | | | |
|---|---|---|---|
| 6,103,275 | A | 8/2000 | Seitz et al. |
| 6,709,681 | B2 | 3/2004 | Benjamin et al. |

FOREIGN PATENT DOCUMENTS

| | | |
|---|---|---|
| EP | 0 630 650 A | 12/1994 |
| WO | WO 95/22335 | 2/1995 |
| WO | WO 99/44622 | 9/1999 |

OTHER PUBLICATIONS

Keratin; [online] retreived from: http://en.wikipedia.org/wiki/Keratin on Jun. 3, 2011; 1 page.*
Shuster, S. Hydroxy-pyridones as antifungal agents 1999, springer, p. 106.*
Prophylaxis; [online] retreived from: http://www.macmillandictionary.com/dictionary/american/prophylaxis on Jun. 3, 2011; 1 page.*
Baran et al. (Manual of nail disease and surgery 1997, Wiley-Blackwell; p. 8).*
Smith et al. (The American Academy of Dermatology 1998, 38(4), 559-563).*
Hardwick et al. Clin Sci., 100, 395-400 (2001).

(Continued)

*Primary Examiner* — Ernst V Arnold
(74) *Attorney, Agent, or Firm* — Fish & Richardson P.C.

(57) ABSTRACT

Nitrogen oxide generating compositions are useful in the treatment of subungual infections, as NO has surprisingly been found to be able to penetrate the nail to exert an antifungal effect.

17 Claims, 13 Drawing Sheets

(56) References Cited

OTHER PUBLICATIONS

Tucker et al. "Effect of nitric-oxide-generating system on microcirculatory blood flow in skin of patient with severe Raynaud's syndrome: a randomised trial." *Lancet.* 354:9191 pp. 1670-1675 (Nov. 13, 1999).

Weller et al. "A randomized trail of acidified nitiric cream in the treatment of tinea pedis." *Journal of The American Academy of Dermatology.* 38:4 pp. 559-563 (Apr. 1998).

Baran, R., "Differential Diagnosis of Onychomycosis and Rationale for a Step-Therapy in Treating Nail Fungal Infection" Chapter 17 in Shuster, S, Ed. Hydroxy-Pyridones as Antifungal Agents with Special Emphasis on Onychomycosis, Springer 1999, pp. 103-109.

\* cited by examiner

GAS PRODUCING FORMULATION

LID OF 2ML EPPENDORF

SABOURAUD DEXTROSE AGAR

ASPERGILLUS NIGER SPORES

KEY

TREATMENT OF NAIL INFECTIONS WITH NO

CROSS-REFERENCE TO RELATED APPLICATIONS

This application is a continuation application of and claims priority to U.S. application Ser. No. 10/484,321, filed on Aug. 2, 2004 now abandoned. This application claims priority under 35 U.S.C. §371 to a national phase filing of international application number PCT/GB02/03575, filed Aug. 2, 2002, which claims priority to GB 0119011.5, filed Aug. 3, 2001. These applications are incorporated by reference herein.

The present invention relates to methods of treatment of infections of finger and toe nails, medications for use in such treatment, and methods for the preparation of such medication.

Nail infections are common and, when serious, can be painful and disfiguring, affecting the quality of life of patients. The fungi involved in nail infections are mainly those that cause athlete's foot (or tinea pedis) spreading from the toe cleft to the nail. Fungal infection of the nail is known as onychomycosis, which is also known as tinea unguium, dermatophytic onychomycosis or nail "ringworm".

The most frequently isolated pathogens in onychomycosis are dermatophytes, especially *Trichophyton rubrum* (toe nails 56%, finger nails 36%) and *Trichophyton mentagrophytes* (toe nails 19%, finger nails 11%). Yeast infections are less common but are usually associated with *Candida albicans* (toe nails 10%, finger nails 30%).

It is estimated that at least 15 to 20% of the population aged 40 to 60 has onychomycosis, with 25 to 40% of those over 60 years suffering this condition, but only 3% or less of under 18's. However, it is difficult to put a precise figure on the actual occurrence of onychomycosis, as at least 50% of sufferers fail to seek medical advice.

Mild onychomycosis may simply be restricted to white patches or pits in the nail's surface but, in more established disease, the symptoms include nail bed hyperkeratosis, nail plate thickening, discolouration and onycholysis (separation of the nail plate from the nail bed).

Many factors predispose patients to onychomycosis, including diabetes mellitus, increasing age, hyperhydrosis, onychogryphosis, trauma, poor peripheral circulation and immunosuppression. It is more common in men, and is rare before puberty and in pre-menopausal women.

Onychomycosis is a fungal condition, and conditions which suit fungal growth tend to encourage the development of onychomycosis. Accordingly, 80% of cases involve the foot, especially the hallux, or big toe, and are commonly associated with, for example, tight fitting footwear and excessive sweating, such as may commonly be encountered in sporting activity. However, trauma is also a significant aetiologic factor, especially in the toenail, the longest toe being particularly susceptible.

It is not completely certain how the condition is acquired, but onychomycosis is contagious. Infections may come from the spread of the fungi from the skin to the nails or directly from other people with skin or nail infections. In the case of toenail infection, athlete's foot fungus can spread to the nail, nail trauma often being present, thereby allowing entry to the fungus.

Treatments for onychomycosis, despite the prevalence of the disease, are somewhat limited, the condition being highly resistant to topical medication. Topical treatments include Loceryl (amorolfine) and Penlac (ciclopirox), but cure rates are low (<10%), and treatment times long (up to 12 months), due to poor penetration through the nail, as well as poor activity against the causative organisms.

One particular problem with treating onychomycosis and other nail infections is that the infection is generally located in, or proximal to, the nail bed, as well as in the nail itself. Thus, the infection is protected from external attack by the very nail which it is disfiguring. Treatment may include removal of nail material to expose the infectious organisms, although it is undesirable to remove too much of the nail. In addition, duration of treatment is generally up to a year, or longer.

More recently, oral treatments have been developed (terbinafine and itraconazole) that have achieved higher cure rates (~70%) and shorter treatment periods (12-16 weeks). However, there are safety concerns with these newer oral therapies, including liver toxicity, severe skin reactions and drug interactions.

Thus, there is a need for a topical, or transungual, therapy that provides cure rates similar to or better than such oral therapies, but with reduced safety concerns.

Surprisingly, we have now found that nitrogen oxides are capable of penetrating the nail and are effective in the treatment of the causative organisms of subungual infections.

Thus, in a first aspect, the present invention provides a nitrogen oxide generating composition for use in the treatment of subungual infections.

Nitric oxide (NO) is a major product of the compositions of the invention, and is well known to have antimicrobial and wound healing effects [c.f. WO 95/22335; and Hardwick et al., (2001), Clin. Sci., 100, 395-400].

Nitric oxide is synthesised in the body in the vascular endothelium and neurons, as well as in activated macrophages. Relatively high levels of NO are observed in sweat. Although it is not known precisely how NO kills microorganisms, it is speculated that NO serves to disrupt bacterial DNA, or interfere with the function of bacterial enzymes which contain transition metals.

Nitric oxide, for therapeutic use, is most conveniently produced by the reaction of nitrite with an acid, particularly an inorganic nitrite with an organic acid. This results in the production of the molecular form of nitrous acid, which readily dissociates into a molecule of water and a molecule of dinitrogen trioxide, the latter, in turn, dissociating to form NO and nitrogen dioxide. The reactions are shown below.

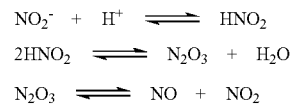

Although $N_2O_3$ is an intermediate in this reaction, there is evidence that it is capable of independent existence, and that it may be at least partially responsible for the fungicidal effects associated with the compositions of the present invention.

In the presence of a reducing agent, such as ascorbic acid, the reaction of dinitrogen trioxide to form NO is more efficient, and can be represented, for example, as follows:

$$N_2O_3 + C_6H_8O_6 \rightarrow 2NO + H_2O + C_6H_6O_6$$

Nitrous acid may suitably be generated, for example, by the action of an acid on a nitrite, particularly where the resulting salt is insoluble.

It will be appreciated that, whilst any suitable source of nitrogen oxides, preferably providing at least a fraction of NO, may be employed in the present invention, it is generally preferred that any nitrogen oxides be generated in accordance with one or more of the above reactions.

The compositions of the present invention may be any that are suitable to provide nitrogen oxides. In one embodiment, the proportion of NO generated by the compositions of the present invention is preferred to be at least 50% and, more preferably, at least 80%. Where the only acid used is a reducing acid, then this proportion may rise to anything up to 100% NO content of the nitrogen oxides generated.

By "nitrogen oxide generating" is meant that compositions of the present invention serve to release nitrogen oxide in situ, i.e. at the location where they are applied, which will generally be on an infected nail. At its simplest, and in one embodiment, this may comprise an ointment or gel or, indeed, any other suitable, topical vehicle, in which gaseous NO has been dissolved, for example, and which, once applied to the nail, releases NO.

Given that only quite small amounts of nitrogen oxides are required in order to be effective, then it does not matter if gas escapes other than at the nail interface, or if only small quantities actually permeate across the nail, or if the amount of nitrogen oxides are attenuated in their passage across the nail, provided that sufficient nitrogen oxides reach the site of action to have a cidal or inhibitory effect.

Although NO and its precursors are generally short lived moieties, with half lives as short as just a few seconds, we have established that they can pass through human nails in sufficient quantities to treat subungual infections. This is all the more surprising, as not only may it may take several hours for there to be any evidence of NO or other nitrogen oxides passing across the nail but, once NO/other nitrogen oxides start to be released, the release can continue for up to 10 hours, or even longer. Without being bound by theory, it appears that the nail is acting as a reservoir, or sink, and adsorbs or absorbs the NO or a precursor therefor. The NO or precursor travels across the nail, and NO and other nitrogen oxides released at the other side. Given the short half lives of the gases, it is possible that they are complexing protein in the nail, and diffusing slowly across.

Although it is known that NO has an antifungal effect, it is not clear that it is necessarily NO that is permeating across the nail, and it may be that NO is only regenerated once the precursor has passed across the nail. Indeed, compositions producing large amounts of NO do not necessarily have the greatest effect in the present invention. Without being bound by theory, it is possible that it is not advantageous to efficiently and quickly generate NO at the surface of the nail, as NO, owing to its short half life, may not diffuse in quantity across the nail. Instead, those compositions taking longer to generate NO appear more efficient at delivering the cidal element across the nail, whether that element be NO or another nitrogen oxide.

Compositions of the invention comprising essentially only ascorbic acid or other similar reducing acid and a nitrite tend to produce large amounts of NO rapidly. Although the nail is somewhat porous, if the NO is produced too quickly there may be insufficient time for the nail to adsorb much of the NO produced, and experiments show that these compositions are associated with a lower overall flux of NO across the nail.

Silver nitrite is capable of producing NO in the presence of acids, but has relatively low efficacy, so is not generally preferred. However, both sodium nitrite and potassium nitrite were found to react with acetic, citric, maleic and malic acid, for example, to produce zones of inhibition in fungicidal tests.

The levels of kill of the fungal mycelium for sodium and potassium nitrite, when combined with acetic, citric, maleic or malic acid, were found to be similar, all giving large zones of inhibition. Likewise, experiments conducted with spores were found to show similar anti-fungal effects for the same acid-nitrite mixtures. General findings were that the solutions produced greater anti-fungal activity compared to creams, whilst mycelia were found to be more susceptible to the anti-fungal effects than spores. However, the creams generally produce nitrogen oxides for longer, which can be an advantage where it is desired to prolong NO or other nitrogen oxide generation at the nail surface to enhance permeation across the nail.

The amount of NO produced by the acid-nitrite mixtures does not necessarily correlate to the size of the zone of inhibition, although there is a general correlation with the overall amount of nitrogen oxides produced. For example, ascorbic acid-nitrite solutions producing large amounts of NO only had little anti-fungal activity in some tests, while potassium nitrite and malic acid combinations only produce approximately half the amount of NO as citric acid, yet the sizes of zones of inhibition were not necessarily any smaller.

The delayed release of nitrogen oxides from the far side of the nail is particularly useful, as it generally takes at least 5 minutes exposure to the active substance to produce kill. Peak killing is observed at around 30 minutes, although anti-fungal activity generally continues to increase up to 2 hours after exposure to the active gas.

The nitrogen oxide generating composition may take any suitable form. However, it will be appreciated that, where the generation of nitrogen oxides is active, then the reactants should be kept separate one from the other until nitrogen oxide is actually required. Although this is generally a preference, it need not necessarily always apply. For example, an occlusive patch may be constructed with a gel, or matrix, into which nitrogen oxide generating ingredients are loaded, the patch then being protected by a suitable webbing to prevent gaseous release.

In such a patch, it is preferred that the matrix or gel is adhesive, and that the strength of the adhesion is sufficient to overcome any tendency of the nitrogen oxide to escape and push away the webbing, although it will be appreciated that the strength of the adhesive should not be such that the webbing cannot be satisfactorily removed to allow application of the patch. Further, it is preferred to provide suitable stabilisers, such as chelating agents, in the gel or matrix, in order to prolong the life of the NO or to reduce the rate at which it is produced. Additionally, as NO is more soluble in non-aqueous and lipid substances, the addition of such substances to the treatment may prolong the activity and delivery of NO to the affected nail and nail bed.

Nevertheless, compositions already comprising free NO will not generally be stable for any great length of time, and should preferably be used by the patient as soon as possible after preparation.

More preferred is to provide the compositions of the present invention in multiple parts. These parts may each, separately, comprise actives or reactants, which, when mixed, serve to generate nitrogen oxides. Thus, a first composition may comprise a suitable nitrite provided in a suitable vehicle. A second composition may comprise a suitable acid. The two compositions can then be mixed, preferably intimately, and then applied to the infected nail, or may be mixed in situ. Although it is generally desired to minimise the number of components that it is necessary to mix in order to achieve the final nitrogen oxide generating composition, it will be appreciated that any number may be provided. In particular, it may be preferred to provide a third composition comprising a reducing acid, for example. However, where a reducing acid, such as ascorbate, is used, then it is generally preferred to either use it as the acid, in its own right, or to provide it together with the primary acid in a separate composition from the nitrite.

The nitrite component may be incorporated in a range of excipients, including, for example, Eudragit L100, carbopol, carboxymethylcellulose, or hydroxymethylcellulose, and the acid component may be incorporated in another suitable excipient, such as carbopol, carboxymethylcellulose, hydroxymethylcellulose, methylcellulose or in an aqueous base. Other excipients, such as polyvinyl alcohol, propylene glycol, polyvinylpyrrolidone (povidone), gelatin, guar gum, and shellac have use in assisting film formation, useful to maintain the composition in situ.

In particular, compositions suitable for introducing substances across the dermis and the stratum corneum may not be generally suitable for the nail, as the nail is effectively a hydrophilic substance, while the stratum corneum is generally hydrophobic. Thus, ionic and ionisable substances readily soluble in water may preferably achieve uptake in the nail, and excipients encouraging this are preferred.

It is generally preferred to use aqueous based formulations to assist in permeation. Such formulations may be mobile solutions but, as it appears that a certain minimum length of exposure of NO and/or other nitrogen oxides to the nail is optimal, then it is generally preferred that any generation of nitrogen oxides does not finish too quickly, in order to allow sufficient time for uptake at the nail interface, and it is generally preferred the formulations be in the form of gels, creams, lotions, ointments, or other thickened form, such as lacquers. Suitable thickening and other characteristics may be achieved by the use of suitable excipients, as described above. For example, it has been established that Eudragits have the ability to alter the release profile of nitrogen oxides from a formulation.

In a preferred embodiment, the composition comprises separate aqueous preparations of an organic acid and a nitrite. More preferably, each preparation is in the form of a gel, cream, lotion, ointment or paint suitable for mixing with the other, which is also selected from a similar group. It is particularly preferred that one or both preparations comprises an excipient suitable to retard the release of nitrogen oxides on mixing. In the case of nitrite, a preferred excipient is a Eudragit, such as Eudragit L100. Other preferred excipients for both are as exemplified above.

The excipients chosen may simply be in order to delay oxide release, but will generally also possess thickening qualities, amounts of the excipient being generally determined by the amount needed to provide a suitable gel. This may vary within well known limits, as readily determined and recognised by those skilled in the art. However, as a guide, suitable amounts may vary between about 1% and about 40%, although there is a large discrepancy between excipients. In general, the preferred excipients need only be used in amounts of between 2% and 10%, such as 3% to 5%, while those used primarily for gelling will be used in amounts suitable to achieve that purpose, whether in combination, or separately. For example, polyethylene glycol is suitably used as a viscosifying agent in amounts ranging from about 10% to 50%, but more preferably about 20% to 35% w/v. Suitable thickening agents include carbopols and the cellulose derivatives, and these are typically employed in amounts of between about 2% and 10%, according to the nature of the formulation required. A preferred formulation is a mobile gel.

It will be understood that the compositions of the invention may comprise other components as desired, such as antioxidants, preservatives, colourants and perfumes, as well as surface active agents and/or penetrating agents, as desired, although aqueous combinations of nitrite and acid are readily able to provide nitrogen oxides across the nail without any need for such additional components.

Although the present invention is generally illustrated herein in respect of two compositions being mixed to provide the final, nitrogen oxide generating composition, it will be appreciated that such references include references to more than two initial compositions, unless otherwise apparent, or indicated.

Compositions of the present invention may comprise any suitable vehicles for mixing. What is important is that the acid and the nitrite, or nitrite precursor, be able to react in such a manner as to generate the desired nitrogen oxides. Thus, at least one of the initial compositions providing the final composition should preferably comprise an aqueous component, in order to allow the nitrogen oxide generating reaction to take place. More preferably, both of the initial compositions should comprise aqueous components to facilitate the mixing of the ingredients although, where it is desired that the ingredients should only react slowly, the amount of water may be minimised in one or both of the initial compositions.

There is no restriction on the types of initial compositions that may be mixed in order to achieve the final composition, provided that the final composition serves to generate nitrogen oxides. In this respect, and throughout, it will be appreciated that reference to "nitrogen oxides" includes reference to 100% NO, although this is not necessarily desirable or preferred.

For example, the initial compositions may be in any suitable form, such as liquid, gel or solid although, where one is solid, then the other is preferably liquid or gel. In the category of liquid, are included solutions, suspensions and colloids, and such considerations also apply to gels, which generally comprise any state between liquids and solids.

More particularly, gels include such states as creams, ointments, tinctures, waxes and lotions, although the latter may fall under liquids, depending on the properties thereof. It will be appreciated that there is no specific exclusion, provided that the liquid gel solid serves as a vehicle for the active.

Solid vehicles may include matrices in patches, for example, or longer chain waxes.

The initial compositions may suitably be mixed, either before application or in situ, in order to provide the final composition to generate nitrogen oxides. Such mixtures may be straightforward gel/gel mixtures, for example, which can then be applied to the nail, and left in place. They may also comprise two liquids which, between them, form a gel, lacquer, solid or paint and, likewise, two gels, or a liquid and a gel, may serve to solidify, form a lacquer, or otherwise form a protective environment to generate, hold and dispense nitrogen oxides.

In one preferred embodiment, a gel may be applied to the nail and then a patch, such as a plaster, carrying a matrix containing the other active is applied over the gel and, once in contact, the actives slowly interact to generate nitrogen oxide.

In another preferred embodiment, the actives may be dispensed as paints or lacquers. Suitably, one component, the nitrite for example, may be applied and allowed to dry, and then the second painted on top. The water in the second allows the reaction to proceed. If desired, a quick drying solvent, such as an alcohol or acetate, may be employed, although it is an advantage of the present invention that such solvents and permeation enhancers are not necessary. It may be desirable, however, to provide ingredients of a film in the separate preparations, so that a polymerisation reaction occurs, for example, on mixing. A catalyst may be provided in one preparation, while a selection of polymerisable monomers may be provided in the other. Alternatively, evaporation of the solvent may allow a polymer in the preparation to gel further, or harden.

The nitrogen oxide generating phase of the compositions of the invention is generally on the wane by two or three hours, and frequently less, although the sinking effect of the nail provides nitrogen oxides at the other side of the nail for considerably longer than this, and often not until oxide production has effectively ceased. During oxide production, it is preferred to keep the blended composition in situ, which may be achieved by the composition setting. Alternatively, it may desirable to protect the nail with an occlusive dressing, for example.

In another preferred embodiment, the matrix of the patch, or plaster, is non-aqueous but hydrophilic, and contains a mixture of the actives in substantially dry form. In this case, the term "dry form" may include crystals incorporating water of crystallisation, for example. Thus, although both of the actives are present in the matrix of the patch, or plaster, they cannot react in the absence of suitable quantities of water to act as solvent to provide a reactive environment. When it is desired to apply the patch, or plaster, any protective webbing can be removed and a suitable quantity of water, such as a few drops, can be applied to the matrix to activate the active ingredients. The activated patch may then be applied to the nail to allow the nitrogen oxides generated to have their effect.

This principle of providing a substantially dry composition to which water is added may also apply to other compositions. In such cases, it will be appreciated that the term "dry" applies to the free water content, so that, whilst a composition may be a gel, for example, the water content will be extremely low, such as 1%, or even lower. It is preferred that such compositions are substantially anhydrous.

The active ingredients of the compositions of the present invention may be present in any suitable quantities, as will be apparent to those skilled in the art. In general, it is preferred that the quantity of nitrite is approximately 0.5 to 30%, by weight, of the final composition. More preferably, the amount of nitrite, or its precursor, is 1 to 20% and, particularly, 1 to 15%, preferably 5 to 15%. A preferred range is 1 to 10%, or 2 to 10%. Higher concentrations are generally preferred, and a minimum concentration of 8-10% is preferred. In creams, lotions and gels, it is envisaged that an upper limit is about 13.5%, although suitable formulation may permit higher levels.

It is generally preferred that the composition of the present invention be provided as two aqueous gels, lotions or creams. More preferably, one contains citric acid at a concentration of between 0.5% and 20%, such as 0.75%, 2.25%, 4.5%, 9% and 13.5% w/w, and the other contains sodium nitrite as described above, for example, 0.5%, 1.5%, 3.0%, 6% and 9% w/w. Preferred concentrations are in the range of 10% for each active component, this providing a suitable excess of the acid. It is also preferred that both actives be present in at least 2%, preferably 5% w/w or greater, to provide an effective dose of nitrogen oxides across the nail. In a preferred embodiment, the acid is present in an amount of 13.5% and the nitrite at 9% while, in another, each is present in amounts of 10%. The preferred acid is citric acid, while the preferred nitrite is sodium nitrite.

The gels, lotions or creams may be mixed in any suitable quantity, by the patient, for example, to cover the affected part of the toe or finger nails(s). Suitable quantities of each gel, lotion or cream may be in the range of 0.05 to 1 g, more preferably 0.1-0.5 g, the components reacting to produce nitrogen oxides.

It is preferred that the acid be present in at least stoichiometric amounts by comparison to the nitrite, or its precursor. More preferably, the acid is present in a stoichiometric excess, sufficient to ensure an acidic environment for a sufficient quantity of the nitrite to generate nitrogen oxides. Although it is not necessary for the whole of the nitrite to generate nitrogen oxides, it is generally inefficient to allow too much of the nitrite to go unreacted, and it is preferred that the majority of the nitrite be converted to nitrogen oxides.

In general, it is preferred that the acid be present in sufficient quantity that the final composition be at a pH of 5, or below, especially pH 4, or below. However, the nitrogen oxide generating reaction may take place a higher pH's, and a pH of 5.5 or even 6 may be acceptable, especially in the presence of excess reducing acids, so that it will be appreciated that the pH of the final composition does not form an essential part of the present invention.

There is no restriction on the nitrite other than that it be generally pharmaceutically acceptable. Even this requirement is not a major consideration, as the final compositions will generally be applied to the nail of the patient, so that dermal contact is minimised, thereby concomitantly minimising potential systemic exposure. Nevertheless, for safety considerations, it is preferred that the nitrites, or their precursors, be generally safe for topical administration.

The nature of the nitrite, for simplicity's sake, will generally be inorganic and at least partially soluble in water. Preferred are the alkali metal nitrites and the alkaline earth metal nitrites, although other suitable nitrites, such as the transition metal compounds, may also be used, subject to suitability, especially solubility. In particular, the sodium, potassium, magnesium and barium compounds may be used, the sodium and potassium compounds generally being preferred from the point of view of expense and availability.

Suitable acidifying agents include inorganic acids but, owing to their general pharmaceutical unacceptability, are not generally preferred. Thus, more preferred are the organic acids, especially those capable of forming a solution with water and yielding a pH of 4 or below. Such acids include formic acid, malic acid, maleic acid, acetic acid, lactic acid, citric acid, benzoic acid, tartaric acid and salicylic acid, and it will be appreciated that this list is inclusive, rather than exclusive. Other suitable acids include ascorbic acid and ascorbyl palmitate which do not necessarily form such acidic solutions, but which are reducing acids and have the advantage of increasing the amount of NO generated, and which may also serve to stabilise the NO, once generated. It will be appreciated that reference to acids herein includes reference to any form of the acid suitable provide an aqueous solution of the acid, either with water alone, or with a, preferably physiologically acceptable deprotecting agent, which may be present initially in the nitrite solution or preparation, prior to mixing. Examples of suitable forms include the hydrated and anhydrous forms of the acid, such as citric acid monohydrate and its anhydrous form.

Owing to the advantageous qualities of the reducing acids, in one embodiment it is preferred to provide a reducing acid in addition to the primary acid when forming the final composition. Suitable proportions are between about 5% and about 200% of the primary acid, with 5% to about 150% more preferred, and particularly between 5 and 40% of the primary acid and, more particularly, between 10 and 20%.

It will be appreciated that the present invention extends to any composition capable of producing a zone of inhibition, in accordance with the accompanying Examples, especially where the organism is *T. rubrum*.

The present invention also extends to methods of treatment of subungual infections wherein the compositions described herein are applied to the infected nail in effective amounts.

The present invention also extends to use of nitrogen oxide generating components in the manufacture of a medicament for the treatment or prophylaxis of a subungual infection.

It will be appreciated that the present invention includes kits of parts comprising compositions as defined herein. In particular, in a preferred embodiment, the present invention provides a kit comprising an aqueous preparation of a nitrite and an aqueous preparation of an organic acid, separately disposed one from the other, the two preparations each being suitable to apply to a nail to be treated such that the nitrite and acid can react to release nitrogen oxides for penetration into the nail. The preparations are preferably in concentrations and/or forms as described herein, especially lotions, gels, creams or lacquers, and are suitably provided in resealable containers such that each kit may provide multiple doses or applications.

Any form of subungual infection may be treated using compositions of the present invention. In general, however, it is preferred to treat onychomycosis.

Suitable durations of treatment will generally be readily determined by the skilled physician. In general, however, it is preferred to continue treatment until either an actual cure or a full, clinical cure is achieved. In the former case, the causative organisms are killed, but the nail may still be disfigured, as finger nails can take 6 months to grow out, while toe nails can take up to a year. A clinical cure is achieved when the affected nail shows no further signs of infection and, as this depends on the nail growing out, can take significantly longer than an actual cure.

It is preferred, in general, to continue treatment for at least two months, more preferably three months, and especially between 3 and 6 months. In fact, our tests indicate that the causative organisms are likely to be killed within a few days of commencing treatment, so that treatment for one week may well be sufficient, especially if compositions are applied two or three times a day, for example. It is envisaged that a three month treatment regimen will be adequate to effect a cure, this also permitting the patient to be able to observe that healthy nail is growing through. However, it will be appreciated that treatment may be continued for as long as desired, for example, until a clinical cure is achieved, which may be up to 14 months or longer, allowing for cure and nail growth.

Doses and amounts of composition to be applied may be dependent on parameters such as the age and weight of the patient but, more particularly, may be dependent on nail dimensions, such as thickness and area, of the recipient, and will be readily determined by the skilled physician. It is an advantage of the present invention that only small amounts of nitrogen oxides are necessary to be effective, so that it is not necessarily a requirement that there be differing prescriptions for different patients, and one type of formulation may be used for all patients. However, different strengths may be employed, such as higher oxide producing formulations for persistent conditions in toes, and lower strength formulations for finger nails, for example. The strength does not necessarily relate to the amount of oxides produced, but may equally relate to the length of time oxides are generated by a given composition.

Administering the compositions of the invention two or more times a day, preferably two or three times a day, forms a preferred embodiment of the invention. This may effectively provide a boost of levels of nitrogen oxides at the infected side of the nail at around the time the effect of the previous dose wears off. Doses may be selected to maintain continuous transfer of nitrogen oxides across the nail, or discontinuous, as desired.

Compositions of the present invention may be made by any suitable means. Where the compositions comprise aqueous components, then it is generally preferred to dissolve the active ingredients in water, or an aqueous preparation, which may then be kept separate from the other actives until required. Any excipients may generally be added after solution of the primary active ingredient. Dry formulations may be made up substantially complete, save for the addition of water, which is added when it is desired to activate the composition.

Where the final composition comprises liquids or gels, these may be applied by any suitable means, including manual mixing. Other means may comprise a double barrelled syringe or a dual actuated dispenser, for example, with final mixing by a finger or spatula, or any other means appropriate.

It will be understood that the following Examples are non-limiting on the present invention. The Examples are illustrated with reference to the accompanying drawings, in which.

METHOD EXAMPLE 1

Analytical In Vitro Model for Screening Gas Producing Formulations

Figure 1:
FIG. 1 illustrates the test used for measuring zones of inhibition.
Figure 1:
Figure 1:
Figure 1:
Figure 1:
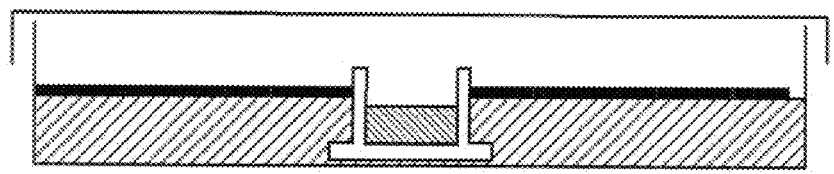

The method for assaying the zone of killing of various creams and solutions was as shown in FIG. 1. The key shows the components of the test. A lid from a 2 ml Eppendorf tube was embedded in a layer of Sabouraud dextrose agar, and the surface of the agar coated with *A. niger* spores. *Aspergillus niger* spores were used, as these are known to be far more resistant to antimicrobial activity compared to the mycelium.

The dishes were either then incubated to obtain a mycelium, or used straight away to test the ability of the mixtures of the invention to kill spores. The mixtures of the invention were placed in the Eppendorf cap and stirred 10 times with the end of a pipette. These test plates are also referred to herein as walled well zone of inhibition plates. Each formulation was tested three times.

This technique provides excellent results, as the NO producing mix does not come into contact with the agar, and controls showed that there was no inhibition of growth by the empty well. This assay is also sensitive.

The controls used were as follows:
i) an empty Eppendorf lid only in Sabouraud dextrose agar;
ii) 0.1 ml sodium nitrite (10%) in an Eppendorf lid;
iii) 0.1 ml citric acid (13.5%) in an Eppendorf lid;
iv) 0.1 ml sodium nitrite (9%) in an Eppendorf lid; and
v) 0.1 ml citric acid (10%) in an Eppendorf lid.

No inhibition of growth was seen with any of the controls.

METHOD EXAMPLE 2

Indicator Organism

The dermatophytes associated with onychomycosis are slow growing organisms taking a minimum of 5 days to produce a full carpet of growth on a Sabouraud dextrose agar plate incubated at 25° C. This is a limiting factor in screening active formulations, as it takes at least a week to produce one set of results. Therefore, it was generally decided to use a faster growing indicator organism to assay the effectiveness of the formulations, although effectiveness of some compositions was confirmed on *T. rubrum*. The organism chosen was the fungus, *Aspergillus niger*, an organism often used to monitor preservative and anti-microbial efficiency of cosmetic and topical formulations.

*A. niger* was used as the indicator organism for fungi associated with onychomycosis, and tests were carried out on both the fungal spores and mycelium. Where the mycelium is used, the killing zone is indicated by the lack of development of fungal spores (black/brown), a white zone showing inhibition of growth. On fungal spore plates, inhibition of growth is indicated by no development of mycelium (white/cream), so that only agar is seen.

METHOD EXAMPLE 3

NO Detection

NO produced was measured using a WPI (World Precision Instruments, Inc.) NO detector. Measurements of NO need to be carried out in an aqueous environment when using this sensor, and the experiments were adapted to suit this requirement. These devices also have the ability to monitor $NO_2$/$NO_3$ production by addition of chemicals and minor modifications of the methods.

Figure 2:
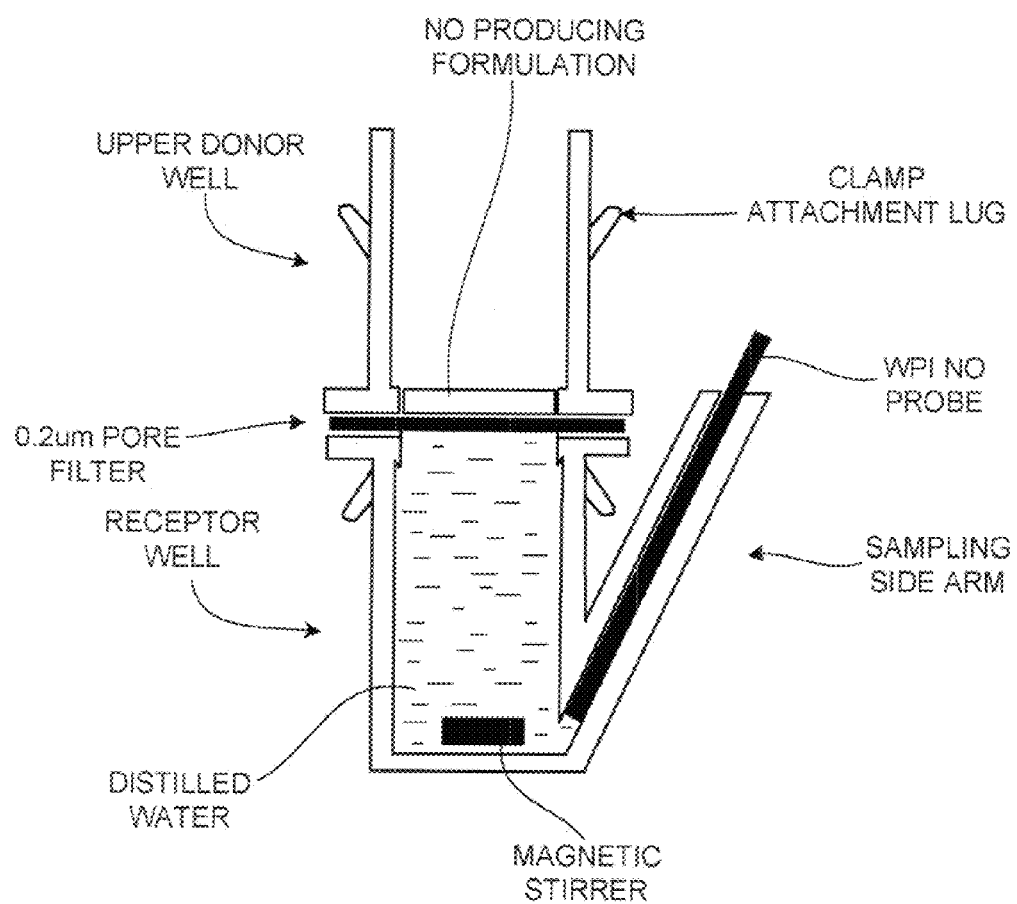
FIG. 2 shows a Franz cell set up to measure evolution of nitrogen oxides from compositions of the invention.

A Franz cell was assembled and positioned onto a magnetic stirrer at room temperature with the de-ionised water in the lower receptor containing a magnetic follower to ensure dispersion of the gas penetrating the membrane. A ½ inch (13 mm) filter paper disk was impregnated with the sodium nitrite component of the NO producing formulation. The impregnated disk was placed in the upper compartment of the Franz cell on top of the membrane before pipetting an equal volume of citric acid component onto it. The amount of NO produced was monitored using the WPI NO probe. The experiment was set up as shown in FIG. 2.

When measured NO levels had reached a plateau, the disk containing the mixture of sodium nitrite and citric acid was removed and 0.1 ml of a 0.1 M $H_2SO_4$+0.1 M KI solution was added to the receptor compartment and the amount of $NO_2$/$NO_3$ was measured (by conversion) using the WPI detector.

EXAMPLE 1

Effect of Acid Preparations Mixed with Nitrite Solutions on *A. niger* Spores

The acids selected were: citric, acetic, ascorbic, maleic and malic acid. The nitrites selected were sodium, potassium and silver.

The assay set up described in Method Example 1 was used. All Examples herein involving zones of killing used the set up of Method Example 1, unless otherwise indicated.

The following acid solutions (w/v) were prepared in distilled water:
1) Citric acid 2.5%
2) Citric acid 5%
3) Citric acid 7.5%
4) Citric acid 10%
5) Ascorbic acid 2.5%
6) Ascorbic acid 5%
7) Ascorbic acid 7.5%
8) Ascorbic acid 10%
9) Maleic acid 2.5%
10) Maleic acid 5%
11) Maleic acid 7.5%
12) Maleic acid 10%
13) Malic acid 2.5%
14) Malic acid 5%
15) Malic acid 7.5%
16) Malic acid 10%
17) Acetic acid 2.5%
18) Acetic acid 5%
19) Acetic acid 7.5%
20) Acetic acid 10%

The lids of 2 ml Eppendorf micro tubes were removed, sterilised and incorporated into a Sabouraud dextrose agar plate, by placing the lids in a petri dish and pouring 25 ml of the agar around them. The agar was allowed to set and was then seeded with *A. niger*. Each of the solutions indicated above were mixed with 2.5, 5, 7.5 and 10% sodium/potassium/silver nitrite solutions by adding exact 0.1 ml quantities of each solution into the lid of the micro tube and mixing by gently rotating the plate. Separate plates were set up for each of the acid solutions listed above and were incubated at 32° C. Zones of inhibition of growth on each plate were measured after 24 hours. The results are shown in Tables 1 and 2, below.

TABLE 1

Sodium Nitrite Zone Of Inhibition Results - *Aspergillus niger* Spores

| | | Sodium nitrite | | | |
|---|---|---|---|---|---|
| | | 2.5% | 5% | 7.5% | 10% |
| Citric acid | 2.5% | 2.2 | 3.0 | 2.9 | 2.8 |
| | 5% | 2.8 | 3.6 | 3.9 | 3.9 |
| | 7.5% | 2.9 | 3.7 | 4.5 | 4.6 |
| | 10% | 3.0 | 4.1 | 4.4 | 5.4 |
| Ascorbic acid | 2.5% | 0 | 0 | 0 | 0 |
| | 5% | 0 | 0 | 0 | 0 |
| | 7.5% | 0 | 0 | 0 | 0 |
| | 10% | 0 | 0 | 0 | 0 |
| Maleic acid | 2.5% | 2.5 | 2.6 | 3.9 | 3.0 |
| | 5% | 3.0 | 3.2 | 3.7 | 3.1 |
| | 7.5% | 3.4 | 3.9 | 4.6 | 4.9 |
| | 10% | 3.1 | 4.4 | 5.1 | 5.8 |
| Malic acid | 2.5% | 2.4 | 2.9 | 3.8 | 3.6 |
| | 5% | 2.9 | 3.4 | 3.8 | 4.2 |

TABLE 1-continued

Sodium Nitrite Zone Of Inhibition Results - *Aspergillus niger* Spores

| | | Sodium nitrite | | | |
|---|---|---|---|---|---|
| | | 2.5% | 5% | 7.5% | 10% |
| | 7.5% | 2.9 | 3.8 | 4.6 | 4.3 |
| | 10% | 3.2 | 4.2 | 5.8 | 5.1 |
| Acetic acid | 2.5% | 2.5 | 2.7 | 3.4 | 3.6 |
| | 5% | 2.8 | 3.3 | 4.0 | 4.0 |
| | 7.5% | 2.6 | 3.5 | 4.1 | 4.1 |
| | 10% | 3.4 | 3.6 | 4.4 | 5.2 |

TABLE 2

Potassium Nitrite Zone Of Inhibition Results - *Aspergillus niger* Spores

| | | Potassium nitrite | | | |
|---|---|---|---|---|---|
| | | 2.5% | 5% | 7.5% | 10% |
| Citric acid | 2.5% | 0 | 0 | 0 | 1.5 |
| | 5% | 0 | 1.5 | 1.8 | 2.8 |
| | 7.5% | 0 | 1.7 | 2.1 | 3.4 |
| | 10% | 0 | 2.2 | 3.2 | 3.8 |
| Ascorbic acid | 2.5% | 0 | 0 | 0 | 0 |
| | 5% | 0 | 0 | 0 | 0 |
| | 7.5% | 0 | 0 | 0 | 0 |
| | 10% | 0 | 0 | 0 | 0 |
| Maleic acid | 2.5% | 0 | 1.3 | 1.5 | 1.4 |
| | 5% | 0 | 2.5 | 3.0 | 2.5 |
| | 7.5% | 0 | 2.5 | 3.2 | 3.2 |
| | 10% | 0 | 3.0 | 3.2 | 5.0 |
| Malic acid | 2.5% | 0 | 1.3 | 1.5 | 1.8 |
| | 5% | 0 | 2.1 | 2.5 | 2.2 |
| | 7.5% | 0 | 2.4 | 2.5 | 2.7 |
| | 10% | 0 | 2.8 | 2.7 | 3.5 |
| Acetic acid | 2.5% | 1.7 | 2.3 | 2.5 | 2.5 |
| | 5% | 2.1 | 3.5 | 3.2 | 4.0 |
| | 7.5% | 3.0 | 3.7 | 4.0 | 4.5 |
| | 10% | 3.5 | 4.0 | 4.5 | 4.6 |

No Table is shown for silver nitrite, as no zones of inhibition were seen for any of the acids tested with silver nitrite.

Some ascorbic acid mixtures swelled on mixing to such an extent that they domed above the tops of the wells, occasionally resulting in small amounts of over-spill on to the agar during transfer of the plates to the incubator, which produced zones of inhibition. No zones of inhibition were seen with ascorbic acid solutions in the absence of spillage. No other acid evinced any sign of over-spill or of swelling. From these tests, it would appear that all mixtures tested, apart from those involving either silver nitrite or ascorbic acid, are effective.

EXAMPLE 2

Effect of Acid Preparations Mixed with Nitrite Solutions on *A. niger* Mycelium

Acid solutions were prepared as described in Example 1. Prior to addition of gas producing formulations, the plates were incubated at 32° C. overnight to establish a full carpet of growth. Solutions were then added to the wells as described in Example 1. The plates were then incubated at 32° C. for a further 24 hours. Zones of inhibition of growth were measured, as the point where the area of spore formation (black), and no spore formation (white/cream) met. Results are shown in Tables 3, 4 and 5.

TABLE 3

Sodium Nitrite Zone Of Inhibition Results - *Aspergillus niger* Mycelium

| | | Sodium nitrite | | | |
|---|---|---|---|---|---|
| | | 2.5% | 5% | 7.5% | 10% |
| Citric acid | 2.5% | 3.0 | 0 | 0 | 0 |
| | 5% | 2.8 | 1.2 | 1.8 | 2.4 |
| | 7.5% | 3.2 | 1.4 | 3.1 | 3.4 |
| | 10% | 3.4 | 3.1 | 3.7 | 4.6 |
| Ascorbic acid | 2.5% | 0 | 0 | 0 | 0 |
| | 5% | 0 (2) | 0 | 0 (2.1) | 0 (2.5) |
| | 7.5% | 0 (2.5) | 0 (3.4) | 0 (2.5) | 0 |
| | 10% | 0 (2.0) | 0 (1.9) | 0 (3.0) | 0 (3.9) |
| Maleic acid | 2.5% | 3.4 | 3.5 | 3.4 | 3.0 |
| | 5% | 3.9 | 4.4 | 4.6 | 4.4 |
| | 7.5% | 4.0 | 5.0 | 4.8 | 6.0 |
| | 10% | 4.2 | 5.4 | 6.2 | 8.0 |
| Malic acid | 2.5% | 3.5 | 3.7 | 3.3 | 3.1 |
| | 5% | 3.7 | 4.2 | 4.1 | 4.1 |
| | 7.5% | 3.5 | 5.0 | 4.9 | 6.0 |
| | 10% | 3.7 | 5.6 | 5.0 | 6.4 |
| Acetic acid | 2.5% | 2.6 | 3.8 | 3.7 | 3.3 |
| | 5% | 3.0 | 3.6 | 3.6 | 4.0 |
| | 7.5% | 3.0 | 4.3 | 4.1 | 4.4 |
| | 10% | 3.6 | 4.5 | 4.7 | 6.2 |

TABLE 4

Potassium Nitrite Zone Of Inhibition Results - *Aspergillus niger* Mycelium

| | | Potassium nitrite | | | |
|---|---|---|---|---|---|
| | | 2.5% | 5% | 7.5% | 10% |
| Citric acid | 2.5% | 2.7 | 3.1 | 3.2 | 3.5 |
| | 5% | 3.1 | 3.9 | 4.2 | 5.0 |
| | 7.5% | 3.6 | 3.9 | 4.2 | 5.4 |
| | 10% | 3.7 | 3.9 | 5.3 | 6.2 |
| Ascorbic acid | 2.5% | 0 | 0 | 0 | 0 |
| | 5% | 0 (1.5) | 0 | 0 (2.0) | 0 (2.4) |
| | 7.5% | 0 (3.1) | 0 (2.5) | 0 | 0 (3.1) |
| | 10% | 0 (2.0) | 0 (2.4) | 0 (3.0) | 0 (3.2) |
| Maleic acid | 2.5% | 3.5 | 3.5 | 3.4 | 3.5 |
| | 5% | 3.8 | 3.8 | 5.0 | 5.0 |
| | 7.5% | 4.1 | 3.9 | 6.5 | 7.8 |
| | 10% | 4.5 | 4.3 | 8.0 | 9.0 |
| Malic acid | 2.5% | 3.4 | 3.9 | 3.8 | 3.4 |
| | 5% | 3.7 | 4.0 | 5.2 | 5.0 |
| | 7.5% | 3.8 | 4.4 | 5.4 | 5.8 |
| | 10% | 4.2 | 5.0 | 6.3 | 6.4 |
| Acetic acid | 2.5% | 2.7 | 2.8 | 3.4 | 3.6 |
| | 5% | 3.4 | 3.0 | 4.2 | 4.4 |
| | 7.5% | 3.6 | 3.7 | 4.3 | 4.7 |
| | 10% | 4.4 | 4.9 | 4.6 | 5.1 |

TABLE 5

Silver Nitrite Zone Of Inhibition Results - *Aspergillus niger* Mycelium

| | | Silver nitrite | | | |
|---|---|---|---|---|---|
| | | 0.025% | 0.05% | 0.075% | 0.10% |
| Citric acid | 2.5% | 0 | 0 | 0 | 0 |
| | 5% | 0 | 0 | 0 | 0 |
| | 7.5% | 0 | 0 | 0 | 0 |
| | 10% | 0 | 0 | 0 | 0 |
| Ascorbic acid | 2.5% | 0 | 0 | 0 | 0 |
| | 5% | 0 | 0 | 0 | 0 |
| | 7.5% | 0 | 0 | 0 | 0 |
| | 10% | 0 | 0 | 0 | 0 |
| Maleic acid | 2.5% | 0 | 0 | 0 | 0 |

TABLE 5-continued

Silver Nitrite Zone Of Inhibition Results - *Aspergillus niger* Mycelium

| | | Silver nitrite | | | |
|---|---|---|---|---|---|
| | | 0.025% | 0.05% | 0.075% | 0.10% |
| | 5% | 0 | 0 | 0 | 0 |
| | 7.5% | 0 | 0 | 0 | 0 |
| | 10% | 0 | 0 | 0 | 0 |
| Malic acid | 2.5% | 0 | 0 | 0 | 0 |
| | 5% | 0 | 0 | 0 | 0 |
| | 7.5% | 0 | 0 | 0 | 0 |
| | 10% | 0 | 0 | 0 | 0 |
| Acetic acid | 2.5% | 0 | 0 | 0 | 1.1 |
| | 5% | 0 | 0 | 0 | 1.2 |
| | 7.5% | 0 | 0 | 0 | 1.2 |
| | 10% | 0 | 0 | 0 | 1.3 |

From these tests, it would appear that all mixtures tested, apart from most of those involving either silver nitrite or ascorbic acid, are effective.

EXAMPLE 3

Effect of Acid Aqueous Cream Preparations Mixed with Nitrite Solutions on *A. niger* Spores The same procedure as described in Example 1 was followed, except that aqueous creams were used in place of solutions, using the same concentrations of both acids and nitrites. The results are shown in Tables 6 and 7.

TABLE 6

Effect of Sodium Nitrite Creams On *Aspergillus niger* Spores

| | | Sodium nitrite | | | |
|---|---|---|---|---|---|
| | | 2.5% | 5% | 7.5% | 10% |
| Citric acid | 2.5% | 0 | 0 | 0 | 0 |
| | 5% | 0 | 0 | 0 | 1.5 |
| | 7.5% | 0 | 0 | 1.6 | 2.3 |
| | 10% | 0 | 0 | 1.7 | 2.9 |
| Ascorbic acid | 2.5% | 0 | 0 | 0 | 0 |
| | 5% | 0 | 0 | 0 | 0 |
| | 7.5% | 0 | 0 | 0 | 0 |
| | 10% | 0 | 0 | 0 | 0 |
| Maleic acid | 2.5% | 0 | 0 | 0 | 0 |
| | 5% | 0 | 0 | 0 | 1.6 |
| | 7.5% | 0 | 0 | 1.7 | 2.2 |
| | 10% | 0 | 0 | 1.9 | 2.5 |
| Malic acid | 2.5% | 0 | 0 | 0 | 0 |
| | 5% | 0 | 0 | 1.2 | 2.0 |
| | 7.5% | 0 | 0 | 1.6 | 2.4 |
| | 10% | 0 | 0 | 1.7 | 2.7 |
| Acetic acid | 2.5% | 0 | 0 | 0 | 0 |
| | 5% | 0 | 0 | 0 | 1.7 |
| | 7.5% | 0 | 0 | 1.7 | 2.3 |
| | 10% | 0 | 0 | 2.2 | 2.8 |

TABLE 7

Effect of Potassium Nitrite Creams On *Aspergillus niger* Spores

| | | Potassium nitrite | | | |
|---|---|---|---|---|---|
| | | 2.5% | 5% | 7.5% | 10% |
| Citric acid | 2.5% | 0 | 0 | 0 | 0 |
| | 5% | 0 | 0 | 1.6 | 1.7 |
| | 7.5% | 0 | 1.7 | 1.65 | 1.8 |
| | 10% | 0 | 1.8 | 1.8 | 1.9 |
| Ascorbic acid | 2.5% | 0 | 0 | 0 | 0 |
| | 5% | 0 | 0 | 0 | 0 |
| | 7.5% | 0 | 0 | 0 | 0 |
| | 10% | 0 | 0 | 0 | 0 |
| Maleic acid | 2.5% | 0 | 0 | 0 | 1.5 |
| | 5% | 0 | 0 | 1.5 | 1.7 |
| | 7.5% | 0 | 0 | 1.6 | 2.0 |
| | 10% | 0 | 0 | 2.3 | 2.9 |
| Malic acid | 2.5% | 0 | 1.4 | 1.4 | 1.6 |
| | 5% | 0 | 1.5 | 2.1 | 1.8 |
| | 7.5% | 0 | 1.65 | 2.3 | 2.3 |
| | 10% | 0 | 1.7 | 2.35 | 2.7 |
| Acetic acid | 2.5% | 0 | 0 | 1.3 | 1.5 |
| | 5% | 0 | 1.3 | 2.0 | 1.7 |
| | 7.5% | 0 | 1.8 | 2.4 | 2.5 |
| | 10% | 1.7 | 2.4 | 2.6 | 2.7 |

No Table is shown for silver nitrite, as no zones of inhibition were seen for any of the acid creams mixed with silver nitrite. From these tests, it would appear that all mixtures tested, apart from those involving either silver nitrite or ascorbic acid, are effective.

EXAMPLE 4

Effect of Acid Aqueous Cream Preparations Mixed with Nitrite Solutions on *A. niger* Mycelium The same procedure as described in Example 2 was followed, except that aqueous creams were used in place of solutions, using the same concentrations of both acids and nitrites. The results are shown in Tables 8, 9 and 10.

TABLE 8

Effect of Sodium Nitrite Creams on *Aspergillus niger* Mycelium

| | | Sodium nitrite | | | |
|---|---|---|---|---|---|
| | | 2.5% | 5% | 7.5% | 10% |
| Citric acid | 2.5% | 0 | 0 | 1.2 | 1.4 |
| | 5% | 0 | 1.2 | 1.4 | 3.1 |
| | 7.5% | 0 | 1.8 | 3.1 | 3.7 |
| | 10% | 0 | 2.4 | 3.4 | 4.6 |
| Ascorbic acid | 2.5% | 0 | 0 | 0 | 0 |
| | 5% | 0 | 0 | 0 | 0 |
| | 7.5% | 0 | 0 | 0 | 0 |
| | 10% | 0 | 0 | 0 | 0 |
| Maleic acid | 2.5% | 0 | 0 | 1.2 | 1.6 |
| | 5% | 0 | 1.3 | 2.7 | 3.2 |
| | 7.5% | 0 | 1.9 | 4.1 | 4.4 |
| | 10% | 0 | 2.1 | 4.4 | 4.5 |
| Malic acid | 2.5% | 0 | 0 | 1.6 | 2.6 |
| | 5% | 0 | 1.2 | 3.1 | 3.5 |
| | 7.5% | 0 | 1.3 | 3.6 | 4.4 |
| | 10% | 0 | 1.65 | 4.3 | 5.2 |
| Acetic acid | 2.5% | 1.2 | 1.3 | 2.0 | 2.4 |
| | 5% | 2.0 | 2.1 | 2.7 | 3.2 |
| | 7.5% | 2.6 | 2.2 | 3.0 | 4.0 |
| | 10% | 2.4 | 3.0 | 3.7 | 4.7 |

TABLE 9

Effect of Potassium Nitrite Creams on *Aspergillus niger* Mycelium

|  |  | Potassium nitrite | | | |
| --- | --- | --- | --- | --- | --- |
|  |  | 2.5% | 5% | 7.5% | 10% |
| Citric acid | 2.5% | 0 | 0 | 0 | 0 |
|  | 5% | 0 | 1.5 | 1.7 | 2.2 |
|  | 7.5% | 0 | 1.8 | 2.1 | 3.2 |
|  | 10% | 1.5 | 2.8 | 3.4 | 3.8 |
| Ascorbic acid | 2.5% | 0 | 0 | 0 | 0 |
|  | 5% | 0 | 0 | 0 | 0 |
|  | 7.5% | 0 | 0 | 0 | 0 |
|  | 10% | 0 | 0 | 0 | 0 |
| Maleic acid | 2.5% | 0 | 0 | 0 | 0 |
|  | 5% | 1.3 | 2.5 | 2.5 | 3.0 |
|  | 7.5% | 1.5 | 3.0 | 3.2 | 3.2 |
|  | 10% | 1.4 | 2.5 | 3.2 | 5.0 |
| Malic acid | 2.5% | 0 | 0 | 0 | 0 |
|  | 5% | 1.3 | 2.1 | 2.4 | 2.8 |
|  | 7.5% | 1.5 | 2.5 | 2.5 | 2.7 |
|  | 10% | 1.8 | 2.2 | 2.7 | 3.5 |
| Acetic acid | 2.5% | 1.7 | 2.1 | 3.0 | 3.5 |
|  | 5% | 2.3 | 3.5 | 3.7 | 4.0 |
|  | 7.5% | 2.5 | 3.2 | 4.0 | 4.5 |
|  | 10% | 2.5 | 4.0 | 4.5 | 4.6 |

TABLE 10

Effect of Silver Nitrite Creams on *Aspergillus niger* Mycelium

|  |  | Silver nitrite | | | |
| --- | --- | --- | --- | --- | --- |
|  |  | 2.5% | 5% | 7.5% | 10% |
| Citric acid | 2.5% | 0 | 0 | 0 | 0 |
|  | 5% | 0 | 0 | 0 | 0 |
|  | 7.5% | 0 | 0 | 0 | 0 |
|  | 10% | 0 | 0 | 0 | 0 |
| Ascorbic acid | 2.5% | 0 | 0 | 0 | 0 |
|  | 5% | 0 | 0 | 0 | 0 |
|  | 7.5% | 0 | 0 | 0 | 0 |
|  | 10% | 0 | 0 | 0 | 0 |
| Maleic acid | 2.5% | 0 | 0 | 0 | 0 |
|  | 5% | 0 | 0 | 0 | 0 |
|  | 7.5% | 0 | 0 | 0 | 0 |
|  | 10% | 0 | 0 | 0 | 0 |
| Malic acid | 2.5% | 0 | 0 | 0 | 0 |
|  | 5% | 0 | 0 | 0 | 0 |
|  | 7.5% | 0 | 0 | 0 | 0 |
|  | 10% | 0 | 0 | 0 | 0 |
| Acetic acid | 2.5% | 0 | 0 | 1.1 | 0 |
|  | 5% | 0 | 0 | 1.8 | 1.2 |
|  | 7.5% | 0 | 1.6 | 2.0 | 1.6 |
|  | 10% | 1.2 | 2.0 | 2.5 | 2.5 |

From these tests, it would appear that all mixtures tested, apart from most of those involving either silver nitrite or ascorbic acid, are effective.

EXAMPLE 5

Amount of NO Produced by Mixtures of Acids and Nitrites

A rough estimation of the amounts of NO produced by each acid and nitrite solution was calculated using the WPI NO probe, as described in Method Example 3. The nitrite component (50 µl) was added to 10 ml of the acid solution in each experiment.

Initially the NO probe was immersed in the acid component (a 10% solution for each experiment). The probe was left to equilibrate in the acid before nitrite was added. Once a baseline had been established, the instrument was zeroed, and the nitrite was added. The lowest concentration was added first, and subsequent additions were made once the curve began to flatten. The graphs produced only provided a rough indication of the amount of NO produced, the values not being measured, on this occasion. A calibration curve was produced prior to each set of readings using the standard protocol detailed by WPI, to allow for any slight changes in NO detection at different temperatures, as suggested by WPI.

For sodium nitrite and potassium nitrite, 2.5, 5, 7.5 and 10% solutions were added at various points to each acid. Silver nitrite is very insoluble and only very low concentrations could be used, so only 0.025, 0.05, 0.075 and 0.1% solutions were added to the acids.

Calibration curves and NO release profiles were generated for all the acids and nitrites. For both sodium nitrite and potassium nitrite mixed with ascorbic acid, bubbles formed around both the magnetic follower and around the NO probe.

A brief study was performed to estimate the relative amounts of $NO_2/NO_3$ in some of the formulations. This was done, as described in Method Example 3 above, by adding 1 ml of 0.1 M $H_2SO_4$ and 0.1 M KI, once the NO producing formulation had reached a maximum. The 0.1 M $H_2SO_4$ and 0.1 M KI converts $NO_2/NO_3$ to NO which is recorded using the WPI NO probe. The results obtained were:

10 ml citric acid (10%)+50 µl $NaNO_2$ (10%) produced 4000 pA of NO.

On addition of 0.1 M $H_2SO_4$ and 0.1 M KI, the peak value reached 20000 pA. It was estimated that there is approximately 20% production of NO with 80% to $NO_2/NO_3$.

10 ml citric acid (10%)+50 µl $KNO_2$ (10%) produced 2200 pA of NO.

On addition of 0.1 M $H_2SO_4$ and 0.1 M KI, the peak reached 10700 pA. It was estimated that there is approximately 20% production of NO, with 80% to $NO_2/NO_3$.

10 ml ascorbic acid (10%)+50 µl $AgNO_2$ (0.1%) produced 5200 pA of NO.

On addition of 0.1 M $H_2SO_4$ and 0.1 M KI, no change was observed in the peak. It was estimated that there was approximately 100% production of NO, with no $NO_2/NO_3$.

10 ml acetic acid (10%)+50 µl $AgNO_2$ (0.1%) produced 70 pA of NO.

On addition of 0.1 M $H_2SO_4$ and 0.1 M KI, the peak reached 2700 pA. It was estimated that there is approximately 3% production of NO, and 97% to $NO_2/NO_3$.

It was surprising to note that, despite the results of the previous Examples, where no zones of inhibition were identified for mixtures employing ascorbic acid, combinations using ascorbic acid appeared to produce considerable amounts of NO. However, ascorbic acid produced little or no $NO_2/NO_3$ with silver nitrite. All of the other acids tested produced larger quantities of $NO_2/NO_3$ than NO.

It is also noteworthy that the malic acid-potassium nitrite NO profile and the citric acid-potassium nitrite NO profile show little correlation between the amounts of NO produced and the zone sizes seen in the earlier Examples. These two acids produced very similar zone sizes, but malic acid produced only approximately a third of the amount of NO with sodium nitrite.

EXAMPLE 6

Formulation Evaluation

Eudragits

Eudragit based lacquers were investigated for their ability to alter the NO release profile of a formulation. Generally, polymethacrylates (Eudragits) are used for oral tablet/capsule formulations as film coating agents. Selection of different films can produce different drug release rates. Different Eudragits available include; Eudragit E, Eudragit L and Eudragit S. Eudragit E is used as a plain insulating film former and is soluble in gastric fluid below pH 5. Eudragits L and S are used as enteric coating agents, and are also resistant to gastric fluid. Different forms of Eudragits L and S are soluble at different pH levels, for example Eudragit L 100 is soluble >pH 6, and Eudragit S 100 is soluble >pH 7. Eudragits can be combined to obtain different drug release characteristics. Investigations were performed on Eudragit formulations containing both acid and nitrite for the production of the active gas.

Eudragit L100 was tested in combination with sodium nitrite and prolonged the release of NO from 5 to 25-30 minutes (data not shown). Formulating the acid component in a reverse Eudragit (E100) appeared to have little or no effect on prolonging the production of NO. Thus, a suitable formulation is sodium nitrite in L100, with the acid component present in abundance in a gel.

EXAMPLE 7

Alternative Gel Formulations

Combinations of nitrite and acid in formulations of various gelling agents were visually assayed. The gelling agents used were as follows:
3% Carboxymethylcellulose (CMC);
3% Methylcellulose (MC);
3% Carbopol 934;
3% Gelatin A;
3% Gelatin B;
20% Polyethylene glycol (PEG) 400;
20% PEG 600;
20% PEG 1000;
3% Hydroxymethylcellulose (HMC); and
3% Polyvinyl alcohol (PA).

All gels were prepared with:
(i) a 10% solution of citric acid, and
(ii) a 10% solution of sodium nitrite.

A visual assessment and a pH test (using litmus paper) were also carried out. Results are shown in Tables 11 and 12.

TABLE 11

10% Sodium nitrite gels

| Gelling agent | pH | Characteristics |
|---|---|---|
| CMC | 8 | Formed thick faint yellow gel |
| MC | 8 | Watery and yellow in colour, also precipitate seen |
| Carbopol 934 | 9.5 | Thick faint yellow opaque gel |
| Gelatin A | 8.5 | Orange clear liquid |
| Gelatin B | 8 | Yellow clear liquid |
| PEG 400 | 8.5 | Faint yellow clear liquid |
| PEG 600 | 8.5 | Faint yellow clear liquid |
| PEG 1000 | 9 | Faint yellow clear liquid |
| HMC | 8.5 | Thick faint yellow gel |
| PA | 8 | Faint yellow liquid, with precipitate |

From Table 11, it can be seen that CMC, HMC and Carbopol all formed stable gels in the presence of 10% sodium nitrite.

TABLE 12

Characteristics of 10% Citric acid gels

| Gelling agent | pH | Characteristics |
|---|---|---|
| CMC | 2 | Mobile gel, opaque (colourless) |
| MC | 1 | Mobile gel, clear |
| Carbopol 934 | 1 | Mobile gel opaque |
| Gelatin A | 2 | Faint yellow clear liquid |
| Gelatin B | 2 | Faint yellow clear liquid |
| PEG 400 | 1 | Clear liquid |
| PEG 600 | 1 | Clear liquid |
| PEG 1000 | 2 | Clear liquid |
| HMC | 1 | Clear thick gel |
| PA | 2 | Clear liquid |

From Table 12, it can be seen that HMC, CMC, MC and Carbopol all formed stable gels in the presence of 10% citric acid.

These tests provide some preliminary indications. In particular, gelatin is a preferred gelling agent, and it is preferred to use this at conventionally higher levels, such as 20% to 40%, more generally around 30%.

EXAMPLE 8

Effects of NO-Producing Formulations on *T. rubrum*

The method described above, in Method Example 2, using a walled well zone of inhibition plate was adapted to test the dermatophyte cidal activity of various NO-producing formulations. The following formulations were made and added to a walled well agar plate, pre-seeded with *T. rubrum*:

Carbopol containing 10% citric acid (50 µl) mixed with the Eudragit L100 containing 10% sodium nitrite (50 µl).
CMC containing 10% citric acid (50 µl) mixed with CMC containing 10% sodium nitrite (50 µl).
Aqueous cream containing 10% citric acid (50 µl) mixed with aqueous cream containing 10% sodium nitrite (50 µl).
HMC containing 10% citric acid (50 µl) mixed with HMC containing 10% sodium nitrite (50 µl).
Eudragit E100 containing 10% citric acid (50 µl) mixed with the Eudragit L100 containing 10% sodium nitrite (50 µl).
MC containing 10% citric acid (50 µl) mixed with the Eudragit L100 containing 10% sodium nitrite (50 µl).
50 µl of 10% citric acid mixed with a solution of 10% sodium nitrite (50 µl).
50 µl of 10% citric acid mixed with the Eudragit L100 containing 10% sodium nitrite (50 µl).
Positive control (no formulation added).

TABLE 13

Results - Zone Sizes After Five Days

NO Producing formulation

| 10% Citric acid | 10% sodium nitrite | Zone of inhibition (cm) |
|---|---|---|
| Carbopol | L100 | 7.7 |
| CMC | CMC | 5.6 |
| Aqueous cream | Aqueous cream | 3.4 |
| HMC | HMC | 8.5 |
| E100 | L100 | 0 |
| MC | L100 | 7.7 |
| Solution | Solution | 8.5 |
| Solution | L100 | 8.5 |
| None | None | 0 |

These results show that *T. rubrum* is highly susceptible to killing by the formulations of the invention, large zones of kill being seen.

EXAMPLE 9

WPI Measurement of NO Production from Lacquers/Gelling Agents

An experiment was set up to analyse the length of time of release of NO from NO-producing formulations. Placing the formulation directly onto the surface of a 0.2 µm pore filter in a Franz cell resulted in the formulations leaching through the filter, with the reactions taking place in the lower reservoir of the Franz cell. Accordingly, antibiotic disks were impregnated with the sodium nitrite component of the NO producing formulation, the disk being placed in the upper compartment of the Franz cell, on top of the membrane, and then pipetting an equal volume of the citric acid component onto the impregnated disk. The amount of NO produced was monitored using the WPI NO probe. The experiment was set up as shown in FIG. 2.

Figure 3:
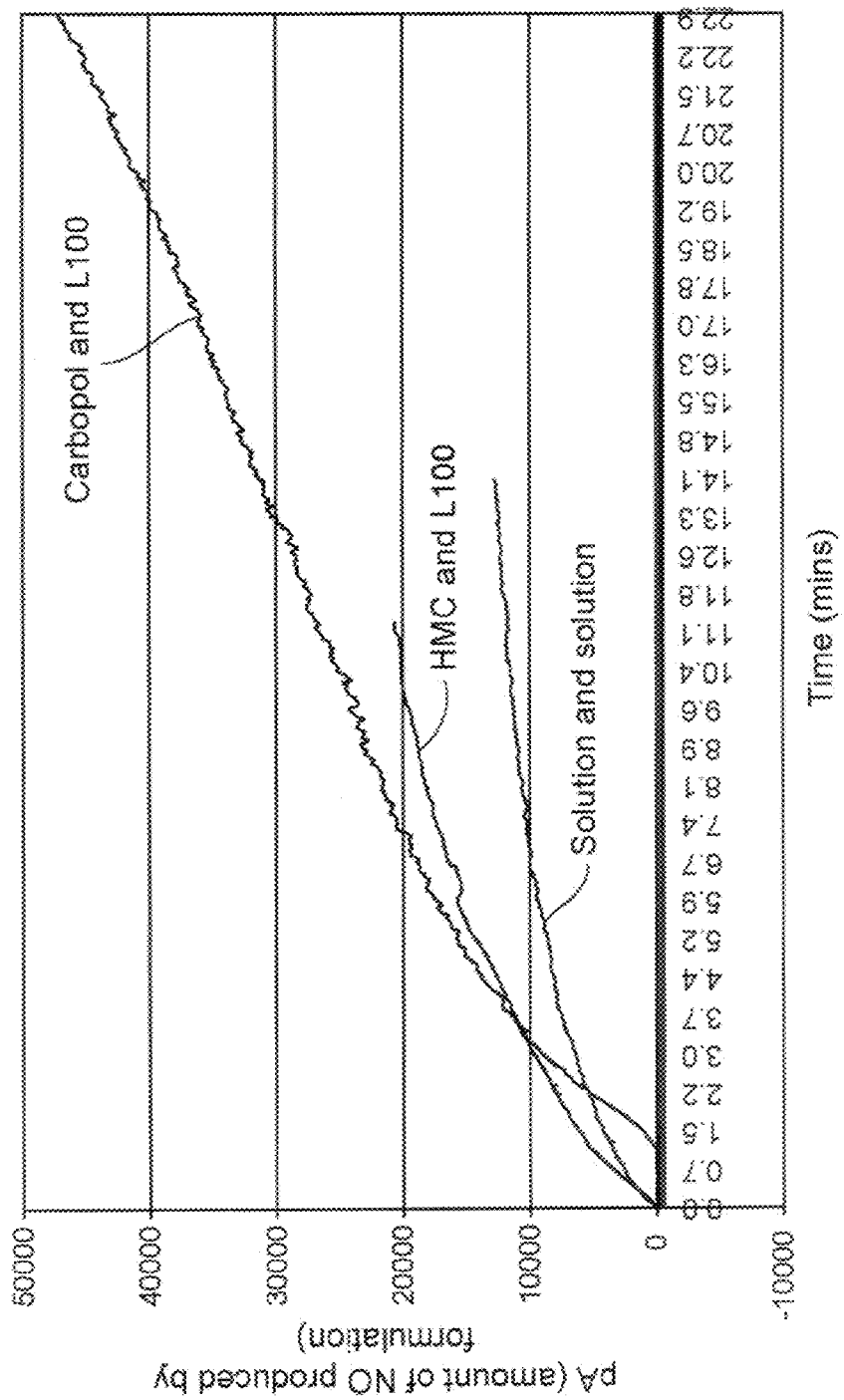
FIG. 3 shows production of NO with respect to time, from a selection of gelling agents containing nitrites and acids.

Three formulations were assessed:
- 10% Citric acid in Carbopol 934 and 10% sodium nitrite in Eudragit L100
- 10% Citric acid in HMC and 10% sodium nitrite in Eudragit L100
- 10% Citric acid in solution and 10% sodium nitrite in solution The results are shown in FIG. 3, which shows production of NO with respect to time, from a selection of gelling agents containing nitrites and acids. The carbopol and L100 NO producing formulation reached a peak at 50000 pA, which is above the detection limit of the WPI meter. However, it can be seen from the graph that this formulation released NO at a fairly steady and at a consistent rate for 23 minutes, at which time the experiment was terminated. By comparison, the NO produced by the solutions began to slow down far earlier, and it is probable that most of the NO produced bubbled out of the solutions and was released into the atmosphere. Similar patterns were seen for the sample with HMC. This shows that a formulation approach can be used to obtain different release profiles of NO.

EXAMPLE 10

Formulation for Testing

The formulations listed in Table 14 were investigated for zone of inhibition, NO release profiles, and $NO_2/NO_3$ release. The concentration of the components listed in Table 14 are those (% w/w in de-ionised water) before mixing.

TABLE 14

| Sample No. | Formulations containing 10% sodium nitrite (% w/w) | Formulations containing 10% citric acid (% w/w) |
|---|---|---|
| 1 | Carboxymethylcellulose (CMC) (3%) + | Carbopol (3%) |
| 2 | CMC (3%) + | Hydroxymethylcellulose (HMC) (3%) |
| 3 | CMC (3%) + | Methylcellulose (MC) (3%) |
| 4 | CMC (3%) + | CMC (3%) |
| 5 | CMC (3%) + | Sol'n (DW) |
| 6 | L100 (Eudragit) (5%) + | Carbopol (3%) |
| 7 | L100 (5%) + | HMC (3%) |
| 8 | L100 (5%) + | MC (3%) |
| 9 | L100 (5%) + | CMC (3%) |
| 10 | L100 (5%) + | Sol'n (DW) |
| 11 | Hydroxymethylcellulose (HMC) (3%) + | Carbopol (3%) |
| 12 | HMC (3%) + | HMC (3%) |
| 13 | HMC (3%) + | MC (3%) |
| 14 | HMC (3%) + | CMC (3%) |
| 15 | HMC (3%) + | Sol'n (DW) |
| 16 | Sol'n (Distilled water (DW)) + | Carbopol (3%) |
| 17 | Sol'n (DW) + | HMC (3%) |
| 18 | Sol'n (DW) + | MC (3%) |
| 19 | Sol'n (DW) + | CMC (3%) |
| 20 | Sol'n (DW) + | Sol'n (DW) |

TABLE 14-continued

| Sample No. | Formulations containing 10% sodium nitrite (% w/w) | Formulations containing 10% citric acid (% w/w) |
|---|---|---|
| 21 | Cream (50% Aqueous cream dissolved in DW) + | Cream (50% aqueous cream dissolved in DW) |
| 22 | Sol'n (DW) + | 1M Sodium ascorbate |
| 23 | Sol'n (DW) + | 1M Sodium hydrogensulphite (SHS) |

The combinations of Table 15 were assessed only for the zone of inhibition.

TABLE 15

| Sample no. | Formulations (% w/w) |
|---|---|
| 24 | citric acid (20%) + ascorbic acid (20%) + sodium nitrite (20%) |
| 25 | citric acid (20%) + ascorbic acid (16%) + sodium nitrite (20%) |
| 26 | citric acid (20%) + ascorbic acid (12%) + sodium nitrite (20%) |
| 27 | citric acid (20%) + ascorbic acid (8%) + sodium nitrite (20%) |
| 28 | citric acid (20%) + ascorbic acid (4%) + sodium nitrite (20%) |
| 29 | citric acid (16%) + ascorbic acid (20%) + sodium nitrite (20%) |
| 30 | citric acid (12%) + ascorbic acid (20%) + sodium nitrite (20%) |
| 31 | citric acid (8%) + ascorbic acid (20%) + sodium nitrite (20%) |
| 32 | citric acid (4%) + ascorbic acid (20%) + sodium nitrite (20%) |
| 33 | citric acid (20%) + 1M $Na_2S_2O_4$ + sodium nitrite (20%) |
| 34 | citric acid (20%) + 1M sodium ascorbate + sodium nitrite (20%) |
| 35 * | citric acid (20%) + 1M $Na_2S_2O_4$ |
| 36 * | citric acid (20%) + 1M sodium ascorbate |
| 37 ** | DW |

The individual components listed represent the initial concentration (% w/w in deionised water (DW)), before mixing.
* and ** represent positive and negative controls, respectively.

Zones of inhibition were also assessed for an alternative reducing agent, α-tocopherol. Combinations for assessment using this agent are listed in Table 16. Formulations containing combinations of sodium nitrite and citric acid with either ascorbic acid (Sample no. 24), $Na_2S_2O_4$ (Sample no. 33) or sodium ascorbate (Sample no. 34) were also included as comparators.

TABLE 16

| Sample no. | Formulation (% w/w) |
|---|---|
| 38 | 9 g DW + 1 g Citric acid + 50 µl α-tocopherol + sodium nitrite (20%) |
| 39 | 4 g DW + 1 g Citric acid + 5 g Ethanol + 50 µl α-tocopherol + sodium nitrite (20%) |
| 40 * | DW + DW |

The individual components listed represent the initial concentrations (% w/w), before mixing.
* represents the negative control.

EXAMPLE 11

A) Zones of Inhibition

Figure 4:
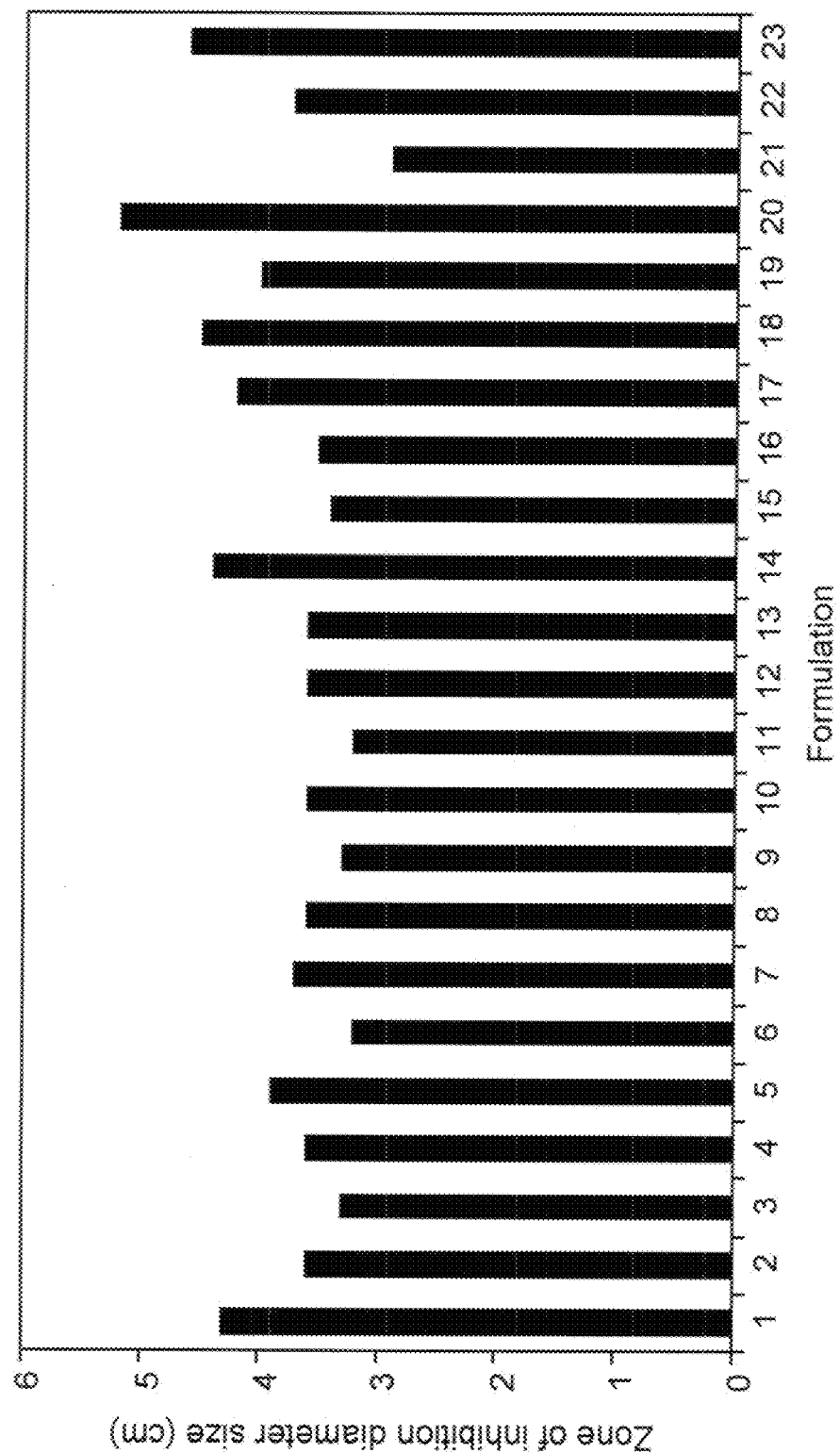
FIG. 4 shows the zones of inhibition for certain solutions and gel based formulations.
Figure 5:
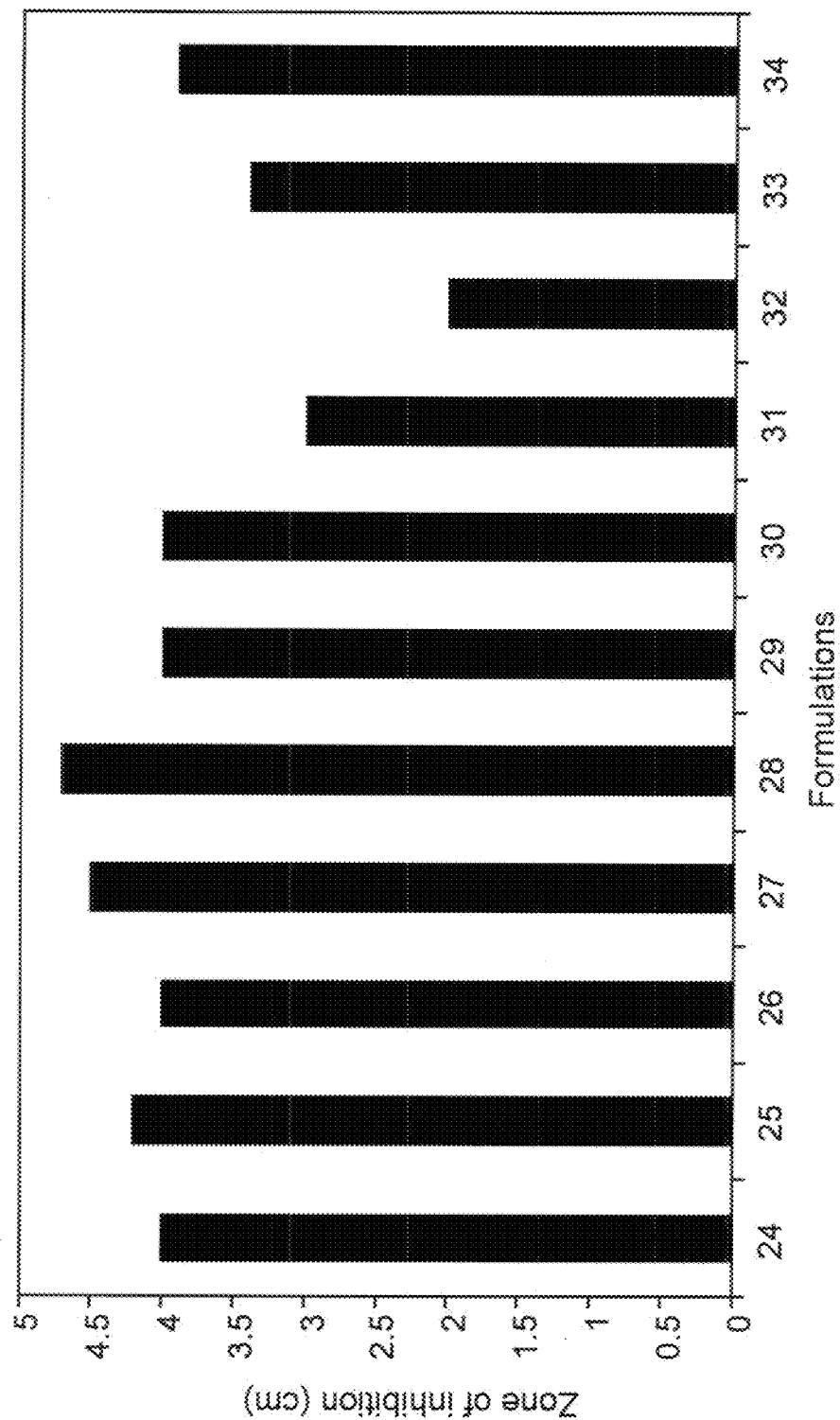
FIG. 5 shows the zones of inhibition for certain formulations investigated in the presence of reducing agents.
Figure 6:
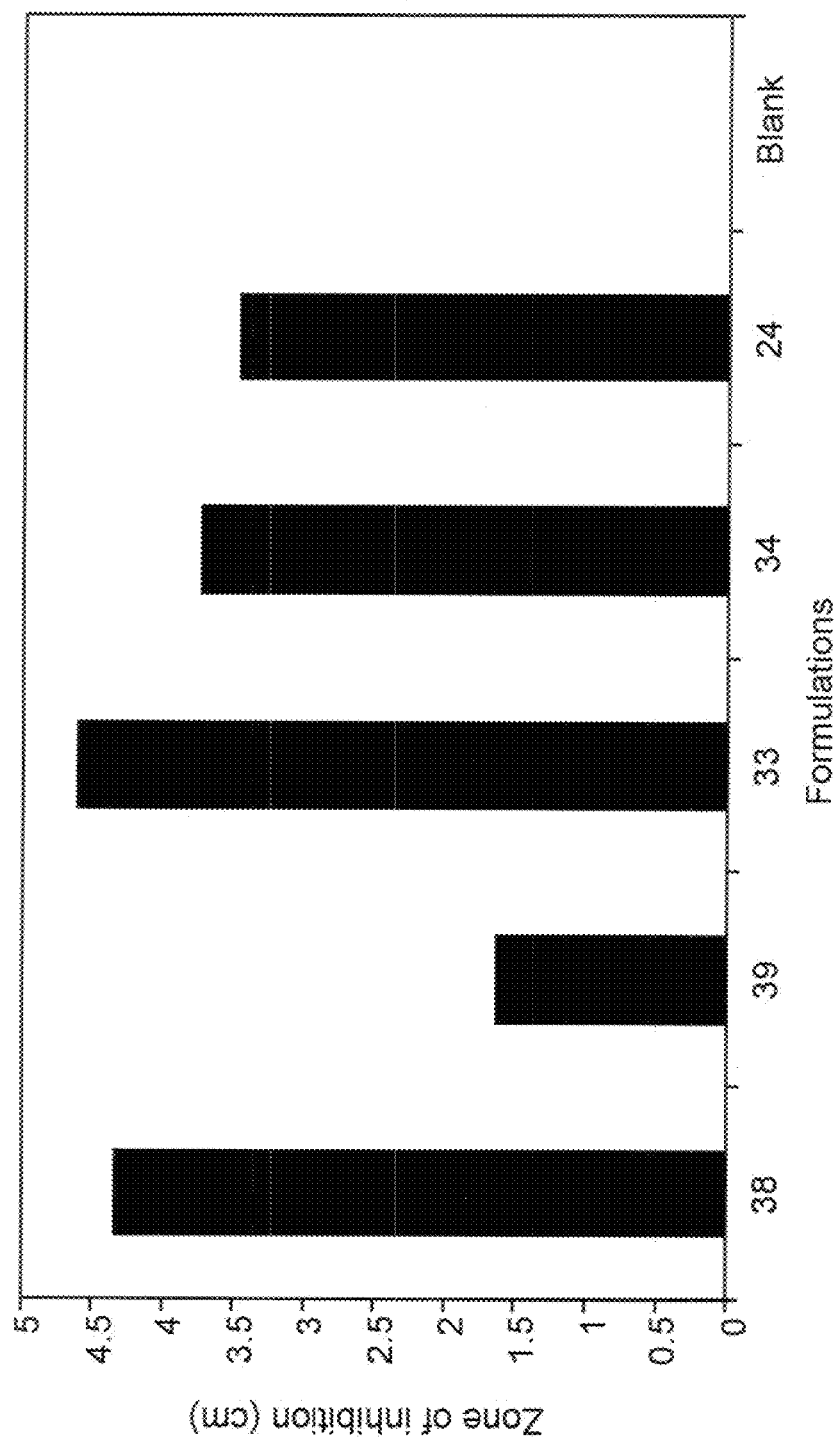
FIG. 6 shows the zones of inhibition for certain formulations investigated in the presence of α-tocopherol and other reducing agents.

FIGS. 4, 5 and 6 show the effect of the formulations of Example 10 on the zone of inhibition. Clearly, it can be concluded that there is no apparent difference in the zone of inhibition observed for most of the formulations investigated, although Sample no. 32 (a low concentration of citric acid with a high concentration of ascorbic acid) and Sample no. 39 (α-tocopherol formulated in ethanol) exhibited lower activity than other formulations. However, other formulations containing combinations of a high concentration (20%) of ascorbic acid (Samples 24-31) showed no apparent reduction in antifungal activity, as shown in the zone of inhibition assay.

FIG. 4 shows the zones of inhibition for solutions and gel based formulations listed in Table 14.

FIG. 5 shows the zones of inhibition for formulations investigated in the presence of reducing agents listed in Table 15.

FIG. 6 shows the zones of inhibition for formulations investigated in the presence of α-tocopherol and other reducing agents listed in Table 16.

B) NO and $NO_2/NO_3$ Release

The data generated from the WPI instrument for the amount of NO produced was quantified in units of pA. A calibration plot was constructed to calculate the concentration of NO released (data not shown). In general, the profiles obtained show that solution based formulations released NO more quickly than gel based formulations. Amongst the solution based formulations, Sample no. 20 (a solution of sodium nitrite and citric acid) showed a high release of NO in the shortest time. However, combinations of solution formulations containing sodium nitrite solution and citric acid in carbopol (Sample no. 16) and CMC (Sample no. 19) appeared to produce the highest amount of NO over an extended period of time. The lowest amount of NO released was generally found to occur with the CMC based formulations.

Figure 7:
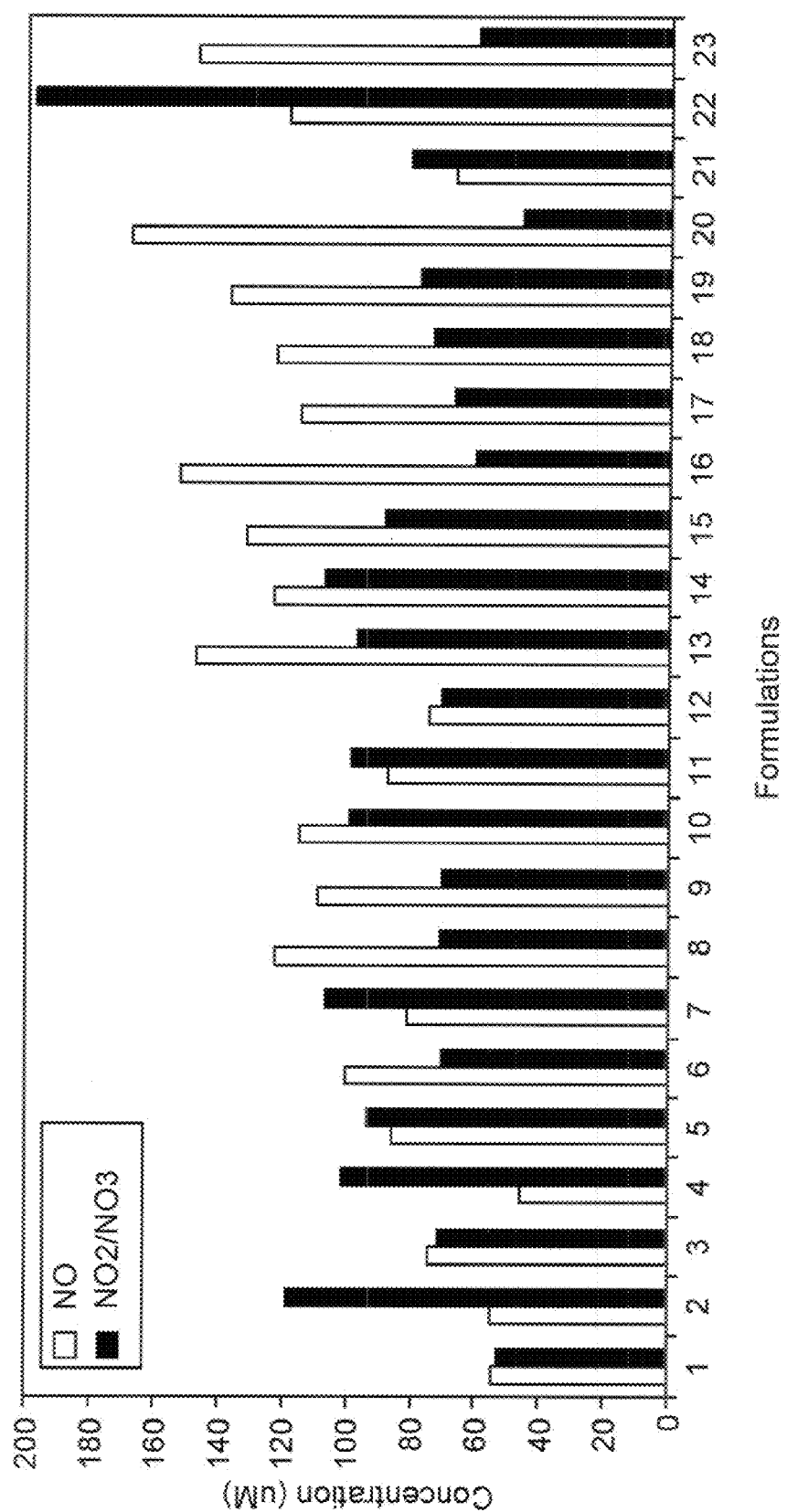
FIG. 7 shows the average peak NO and $NO_2/NO_3$ concentrations produced by various formulations.
Figure 8:
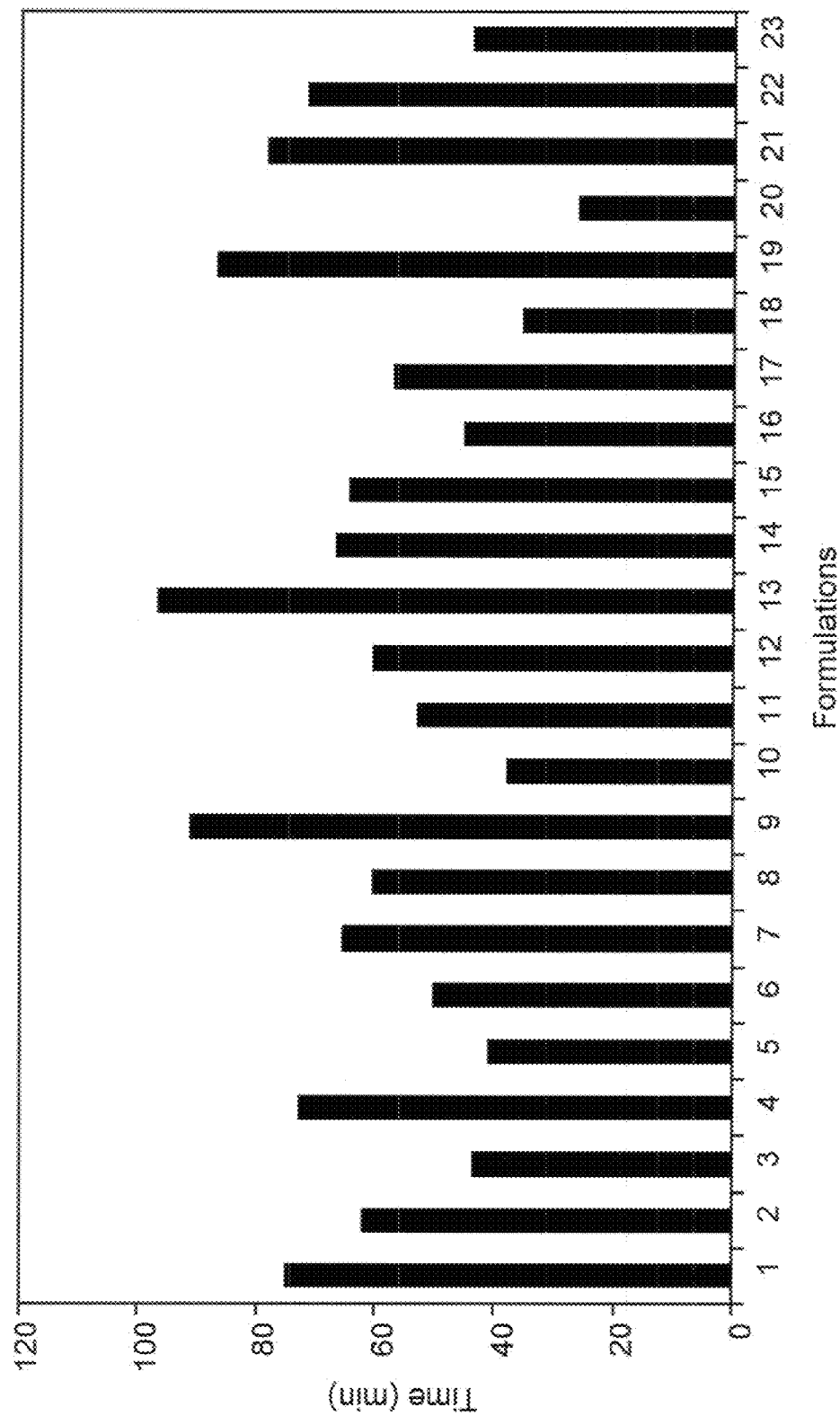
FIG. 8 shows the average time to reach the maximum NO production from the various formulations investigated.

FIG. 7 shows the average peak NO and $NO_2/NO_3$ concentrations produced by the various formulations investigated. Of the gel based formulations investigated, CMC formulations were found to produce lower concentrations of NO compared to the remaining gel based formulations (L100, HMC and Carbopol). The average peak NO concentrations produced as a function of time from the various formulations investigated are shown in FIG. 8. With the exception of Sample no. 19 (which contained CMC) the data demonstrated that the solutions (Sample no. 5, 10, 16-20) were significantly faster in achieving peak NO concentration when compared to the gel formulations.

FIG. 7 shows the average peak NO and $NO_2/NO_3$ concentration produced from the various formulations investigated.

FIG. 8 shows the average time to reach the maximum NO production from the various formulations investigated.

EXAMPLE 12

Passage of NO Across Human Nail 18 h, 10% Solutions

Figure 9:
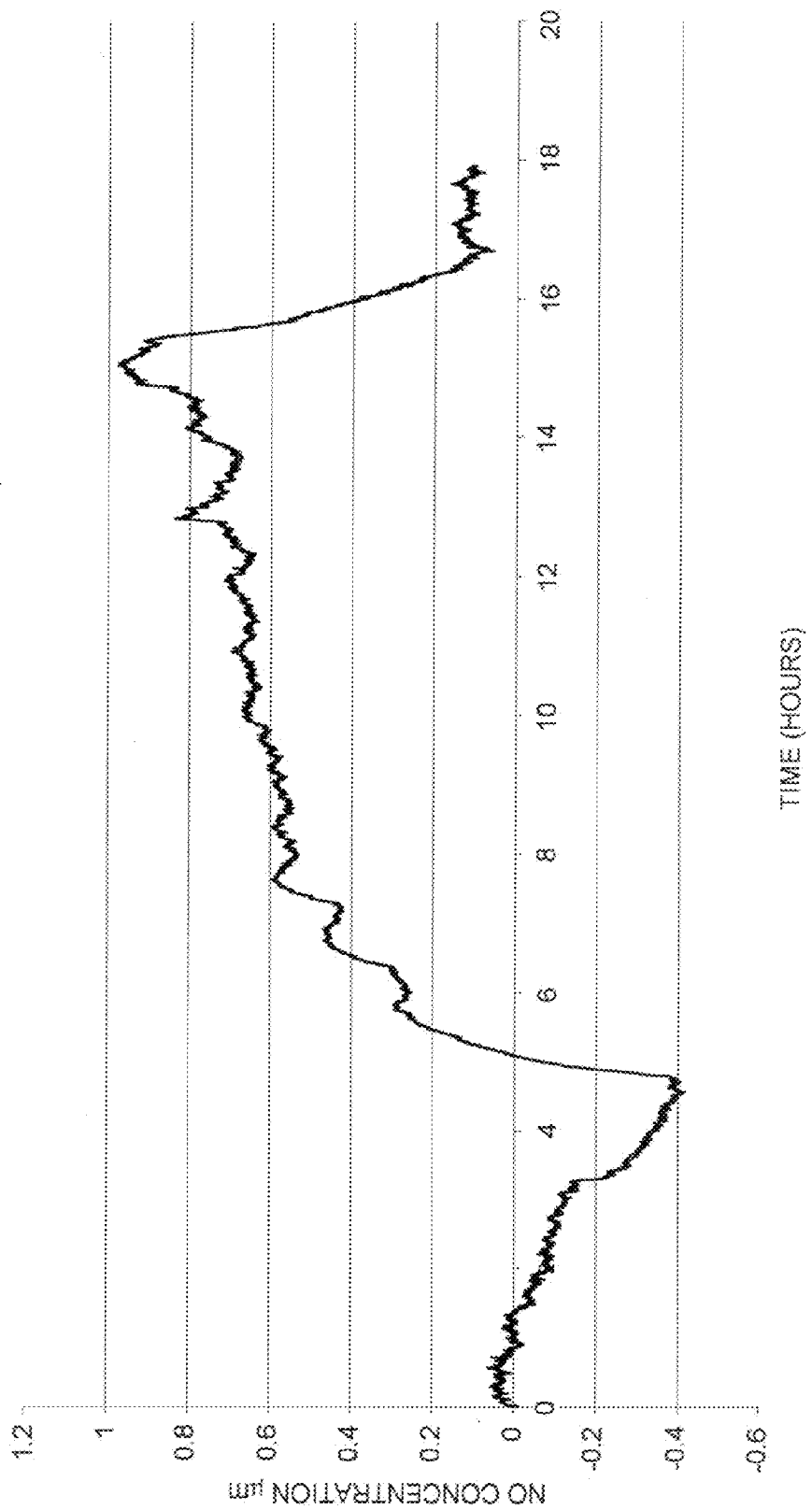
FIG. 9 shows the amount of NO which passed through a nail from 10% acid and 10% nitrite solutions over an 18 hour period.
Figure 11:
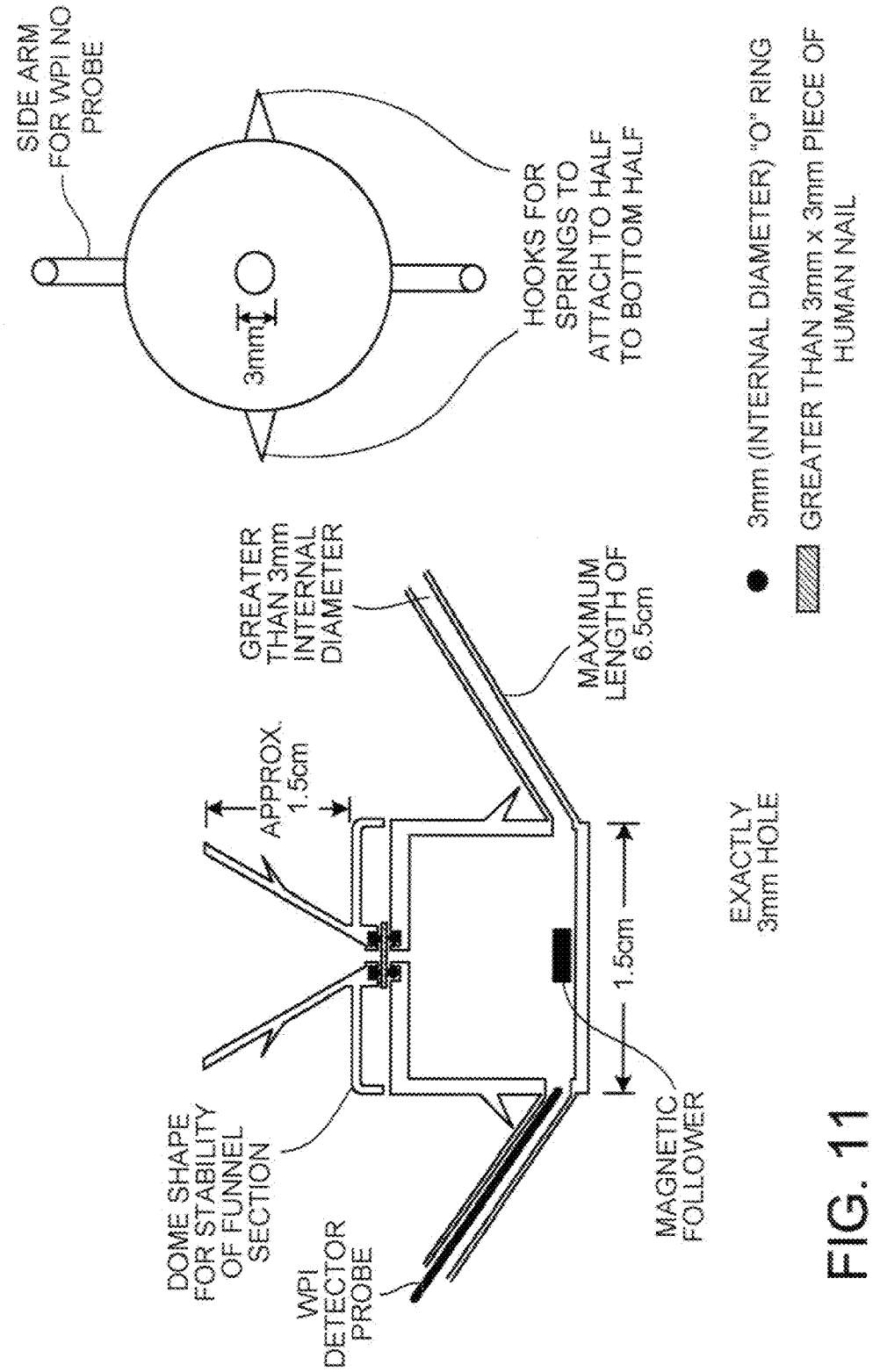
FIG. 11 shows the set up used to measure the amounts of NO passing through the nail in FIGS. 9 and 10.

The set up shown in FIG. 11 was employed. At $T_0$, one application of 100 µl of 10% sodium nitrite and 100 µl of 10% citric acid were pipetted onto the surface of a piece of human nail, mounted in the nail Franz cell (exposure surface 0.1963 $cm^2$). The amount of NO which passed through the nail was monitored using the WPI NO detector, over an 18 hour period. The results are shown in FIG. 9.

18 h, 5% Solutions

Figure 10:
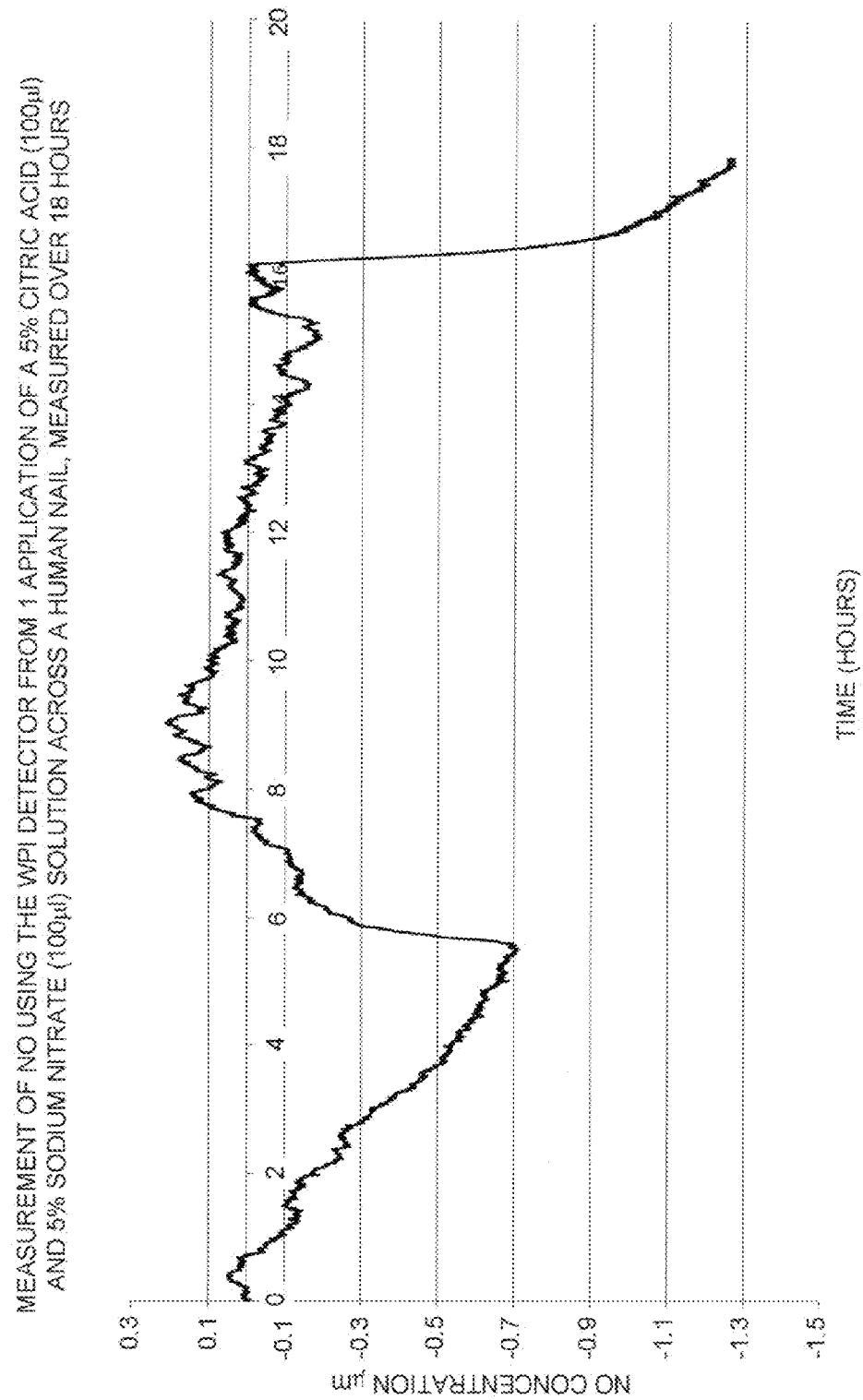
FIG. 10 shows the amount of NO which passed through a nail from 5% acid and 5% nitrite solutions over an 18 hour period.

The set up shown in FIG. 11 was employed. At $T_0$, one application of 100 µl of 5% sodium nitrite and 100 µl of 5% citric acid were pipetted onto the surface of a piece of human nail, mounted in the nail Franz cell (exposure surface 0.1963 $cm^2$). The amount of NO which passed through the nail was monitored using the WPI NO detector, over an 18 hour period. The results are shown in FIG. 10.

Negative Control

The negative control comprised 200 µl of de-ionised water pipetted onto the surface of a piece of human nail, mounted in the nail Franz cell, otherwise employing the same conditions as for the 10% and 5% procedures.

As can be seen from the Figures, the 10% solutions provided an apparent initial drop in NO. However, after about 4 hours (different experiments yield different lag times, data not shown), NO abruptly increases and is then maintained at high levels for a period of about 10 hours. The 5% solutions produced positive levels of NO, albeit somewhat lower than the 10% formulations. The negative control never deviated from the baseline, after an initial dip at the beginning of the experiment (data not shown).

EXAMPLE 13

Measurement of NO Passage Across Human Nail Using 10% Ascorbic Acid and 10% Sodium Nitrite In the first part of the experiment, the dual arm nail Franz cell of FIG. 11 was set up, but using a piece of gas permeable membrane in place of the human nail. The system was left for approximately 40 min before the formulations were added. 100 µl of 10% ascorbic acid and 100 µl of a 10% sodium nitrite solution were added to the top of the Franz cell as in Example 12, and the top of the Franz cell was covered with parafilm.

The amount of NO produced during this experiment exceeded the detection limit of the NO detector, and the plot went off scale (10 µM) after just over one hour. No initial drop in the peak was observed. The amount of NO produced was approximately 20 times higher than that seen with citric acid (10%) and sodium nitrite (10%).

The experiment was then repeated, this time using a piece of human nail. 100 µl of 10% ascorbic acid and 100 µl of 10% sodium nitrite were then applied directly to the top surface of the nail and mixed. The Franz cell was covered with parafilm, and the amount of NO passing through the nail monitored using the WPI meter. The results are shown in FIG. 12.

The drop in the peak appears to be a standard artefact in experiments involving human nail and NO producing formulations. The increase in the peak following the decrease was very sudden, with no gradual change, from one to the other.

Figure 12:
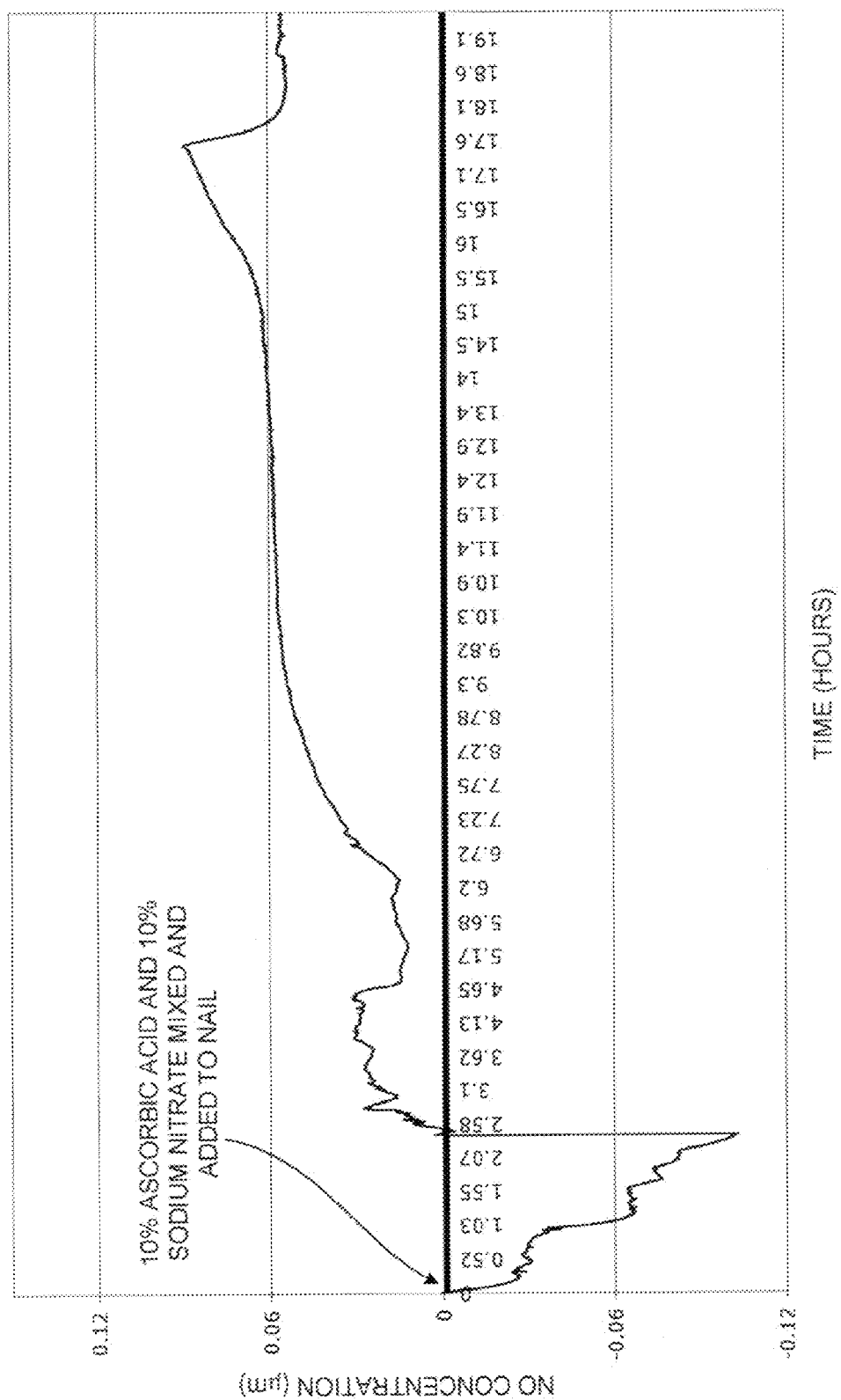
FIG. 12 shows the amount of NO which passed through a nail from a 10% ascorbic acid and 10% nitrite solution over an 18 hour period.

From FIG. 12, it can be seen that, while mixtures involving ascorbic acid can provide sustained release of NO across the nail, the levels are about 10× lower than when using citric acid.

EXAMPLE 14

Franz Cell Nail Bioassay for Anti-Fungal Gas Penetration Across a Human Nail

Figure 13:
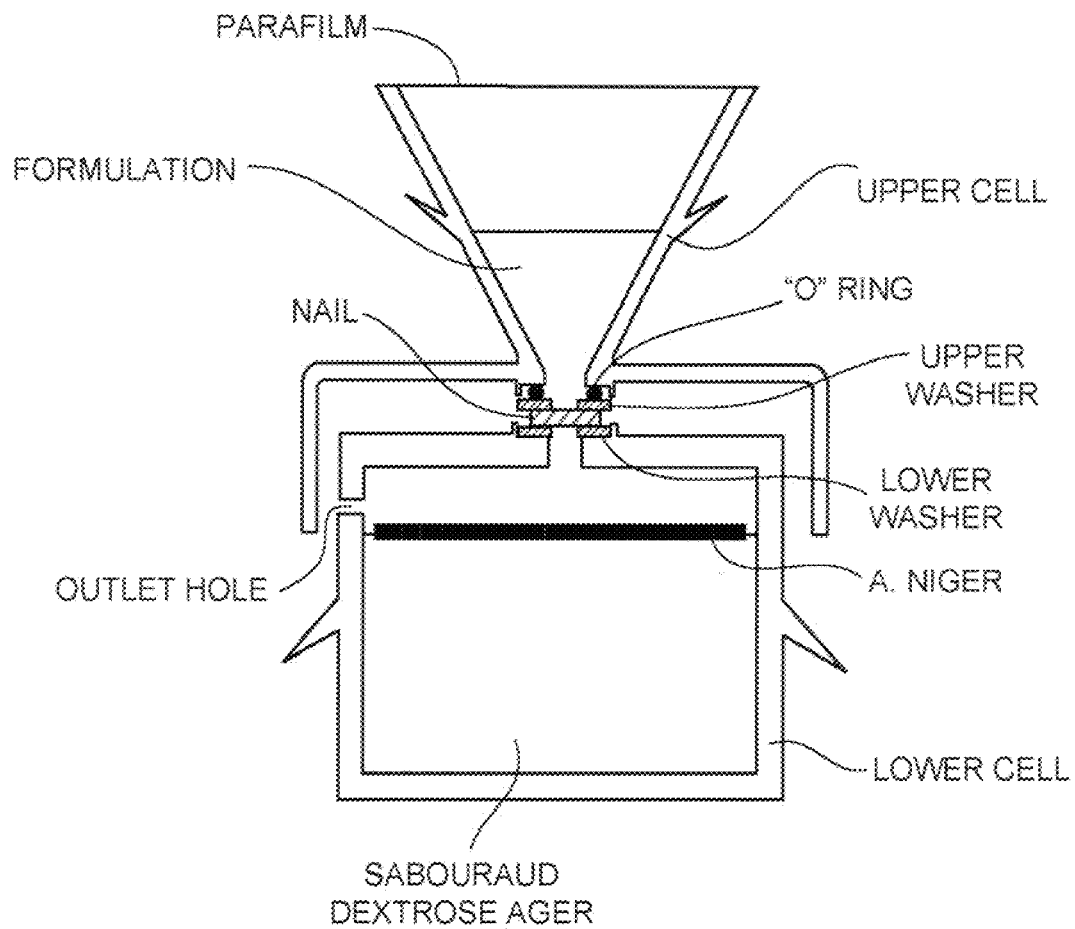
FIG. 13 shows the Franz cell set up used to measure the zones of inhibition achieved by compositions of the invention applied to a human nail.

Franz cells were set up as shown in FIG. 13, the lower section being filled with molten Sabouraud dextrose agar up to 8 mm below the outlet hole. After the agar had cooled and set, 25 µl of an *A. niger* spore suspension was pipetted onto the surface of the agar and a section of human nail fitted in an air-tight manner above the outlet hole, and clamped in place. The cells were then incubated at 32° C. for 24 h to obtain a carpet of mycelium.

Once the mycelium had grown, the cells were removed from the incubator, and 0.1 ml of citric acid and 0.1 ml of sodium nitrite were pipetted into the funnel of the Franz cell and mixed using the pipette tip. Negative controls had either a 0.2 ml solution of 10% sodium nitrite or 0.2 ml of 10% citric acid added. The top of the funnel for all of the Franz cells was then covered with Parafilm. The cells were left at room temperature. After a period of 2 h 10 min, the solutions in each Franz cell were removed and replaced with an equivalent solution and the process repeated every 2 h and 10 min for a further two applications, giving a total of 4 applications. After the final application of solution, the cells were left covered at room temperature, to allow slow growth of the organism for 24 h.

After 24 hours, all six cells with mixtures of citric acid and sodium nitrite had a central region of the colony of *A. niger*, closest to the nail/formulation, which had been killed by the active gas. This was evidenced by a halo effect, where an area of dead, white mycelium was surrounded by a ring of black, sporulating mycelium. After a further 24 hours, the *A. niger* recovered by growing from the outmost region, which was not killed, towards the centre.

All of the cells with either sodium nitrite or citric acid showed a full carpet of growth of mycelium, which had formed spores, as evidenced by a solid black circle.

This result clearly demonstrates the ability of the formulations of the invention to generate an effective gaseous component across a nail. It definitively shows that the active gas is penetrating a complete human toe nail, and directly affecting the growth of *A. niger*. In addition, the formulation is penetrating the nail and affecting the growth of an organism over an additional 8 mm distance, the separation in vivo being virtually negligible. The controls confirm that it is the active gas that is causing the halo effect.

EXAMPLE 15

Kits

A kit comprising two aqueous gel preparations was made up. The preparations had the following formulations:

A. Sodium Nitrite Gel (2 ml)

| | |
|---|---|
| Sodium Nitrite | 6.6% |
| Hydroxymethylcellulose | 10.0% |
| Polyvinyl Pyrrolidone | 5.0% |
| Polyethylene glycol | 20.0% |
| Benzyl Alcohol | 1.0% |
| Colour | 0.005% |
| Water | qs to 100% |

B. Citric Acid Gel (2 ml)

| | |
|---|---|
| Citric acid | 10.0% |
| Carbopol | 5.0% |
| Polyvinyl pyrrolidone | 5.0% |
| Polyethylene glycol | 30.0% |
| Methyl paraben | 0.2% |
| Propyl paraben | 0.02% |
| Water | qs to 100% |
| Colour | 0.005% |

Formulations A and B were separately provided in resealable, squeezable tubes for mixing either immediately before application to the nail, or on the nail itself.

The invention claimed is:

1. A method for the treatment of a subungual infection in a patient, the method comprising:
   generating nitrogen oxide by combining a nitrite and an organic acid, wherein the nitrite and the organic acid are separately disposed from each other prior to being combined, and combining the nitrite and the organic acid forms a composition, wherein the composition is generated on, or applied to, a nail of the patient in an amount that effectively treats an infection under the nail.

2. The method according to claim 1, wherein the organic acid is present in sufficient quantity that the composition formed by combining the nitrite and the organic acid is at a pH of 5.5, or below.

3. The method according to claim 1, wherein the organic acid is selected from: formic acid, malic acid, maleic acid, acetic acid, lactic acid, citric acid, benzoic acid, tartaric acid and salicylic acid, ascorbic acid, ascorbyl palmitate, and mixtures thereof.

4. The method according to claim 1, wherein the nitrite is selected from the alkali metal nitrites and the alkaline earth metal nitrites.

5. The method according to claim 4, wherein the nitrite is selected from: sodium, potassium, magnesium and barium nitrites.

6. The method according to claim 1, wherein the organic acid comprises citric acid and the nitrite comprises sodium nitrite, at least one being present in an aqueous vehicle.

7. The method according to claim 1, wherein the subungual infection is onychomycosis.

8. The method according to claim 1, wherein the nitrite is formulated with an excipient selected from: polymethacrylates, cross-linked polyacrylates, carboxymethylcellulose, hydroxymethylcellulose, and mixtures thereof.

9. The method according to claim 1, wherein the organic acid is formulated with an excipient selected from: cross-linked polyacrylates, carboxymethylcellulose, hydroxymethylcellulose, methylcellulose, and mixtures thereof.

10. The method according to claim 1, wherein the organic acid and the nitrite are separately disposed in aqueous based formulations prior to being combined.

11. The method according to claim 10, wherein each preparation is in a form separately selected from gels, creams, lotions, ointments and paints suitable for mixing each with the other.

12. The method according to claim 1, wherein the organic acid and the nitrite are each separately formulated as a gel, paint or lacquer prior to being combined.

13. The method according to claim 1, wherein, prior to being combined, the organic acid and the nitrite are each separately formulated as a liquid or gel which, when mixed, solidify or form a gel or paint.

14. The method according to claim 1, wherein the nitrite is approximately 0.5 to 30%, by weight, of the composition formed by combining the nitrite and the organic acid.

15. The method according to claim 14, wherein the nitrite is 5 to 15%, by weight, of the composition formed by combining the nitrite and the organic acid.

16. The method according to claim 1, wherein the organic acid is approximately 5 to 30%, by weight, of the composition formed by combining the nitrite and the organic acid.

17. The method according to claim 16, wherein the organic acid is approximately 10 to 15%, by weight, of the composition formed by combining the nitrite and the organic acid.

* * * * *